US011648233B2

(12) United States Patent
Liu et al.

(10) Patent No.: US 11,648,233 B2
(45) Date of Patent: May 16, 2023

(54) **HERIPENES WITH PAIN-RELIEVING EFFECT, ACTIVE SUBSTANCES OF *HERICIUM ERINACEUS* MYCELIUM AND THE PREPARATION METHOD THEREOF, AND PHARMACEUTICAL COMPOSITION CONTAINING THE HERIPENES OR ACTIVE SUBSTANCES**

(71) Applicant: GRAPE KING BIO LTD., Taoyuan (TW)

(72) Inventors: Pei-Shan Liu, Taipei (TW);
Chien-Chih Chen, Taipei (TW);
Chin-Chu Chen, Taoyuan (TW); Li-Ya Lee, Taoyuan (TW); Wan-Ping Chen, Taoyuan (TW); Ting-Wei Lin, Taoyuan (TW); Jui-Hsia Hsu, Taoyuan (TW);
Wei-Ching Chu, Taoyuan (TW)

(73) Assignee: GRAPE KING BIO LTD., Taoyuan (TW)

( * ) Notice: Subject to any disclaimer, the term of this patent is extended or adjusted under 35 U.S.C. 154(b) by 491 days.

(21) Appl. No.: 16/674,209

(22) Filed: Nov. 5, 2019

(65) Prior Publication Data
US 2020/0068815 A1 Mar. 5, 2020

Related U.S. Application Data

(63) Continuation of application No. 15/508,369, filed as application No. PCT/CN2015/088813 on Sep. 2, 2015, now abandoned.

(51) Int. Cl.
| | | |
|---|---|---|
| *A61K 31/343* | (2006.01) | |
| *C07D 493/06* | (2006.01) | |
| *C12N 1/14* | (2006.01) | |
| *A61K 9/14* | (2006.01) | |
| *A61K 36/07* | (2006.01) | |
| *C12P 17/18* | (2006.01) | |
| *C12R 1/645* | (2006.01) | |

(52) U.S. Cl.
CPC .............. *A61K 31/343* (2013.01); *A61K 9/14* (2013.01); *A61K 36/07* (2013.01); *C07D 493/06* (2013.01); *C12N 1/145* (2021.05); *C12P 17/181* (2013.01); *A61K 2236/11* (2013.01); *A61K 2236/33* (2013.01); *A61K 2236/331* (2013.01); *A61K 2236/53* (2013.01); *C12R 2001/645* (2021.05)

(58) Field of Classification Search
CPC ..... A61K 36/07; A61K 31/343; C12P 17/181; C12N 1/145
See application file for complete search history.

(56) References Cited

FOREIGN PATENT DOCUMENTS

| | | | | |
|---|---|---|---|---|
| CN | 101455354 A | | 6/2009 | |
| CN | 101829159 A | * | 9/2010 | |
| CN | 103651657 A | | 3/2014 | |
| CN | 104072593 A | * | 10/2014 | ........... C07K 14/375 |
| CN | 104497059 A | | 4/2015 | |
| JP | 2010235463 A | | 10/2010 | |
| JP | 2014223051 A | * | 12/2014 | |
| TW | 201437371 A | | 10/2014 | |

OTHER PUBLICATIONS

Collier et al., "Antagonism by Aspirin and Fenamates of Bronchoconstriction and Nociception induced by Adenosine-5'-triphosphate," Nature, vol. 212, Oct. 22, 1966 (pp. 411-412).
Cockayne et al., "Urinary bladder hyporeflexia and reduced pain-related behaviour in P2X3-deficient mice," Nature, vol. 407, Oct. 26, 2000 (pp. 1011-1015).
Souslova et al., "Warm-coding deficits and aberrant inflammatory pain in mice lacking P2X3 receptors," Nature, vol. 407, Oct. 26, 2000 (pp. 1015-1017).
Jarvis et al., "Antagonism of P2X3-containing channels: commentary to Spelta et al.," British Journal of Pharmacology (2002) 135, 1343-1344.
Tsuda et al., "P2X4 receptors induced in spinal microglia gate tactile allodynia after nerve injury," Nature, vol. 424, Aug. 14, 2003 (pp. 778-783).
Khakh et al., "P2X receptors as cell-surface ATP sensors in health and disease," Nature, vol. 442, Aug. 3, 2006 (pp. 527-532).
Burnstock, "Purinergic signalling and disorders of the central nervous system," Nature Reviews, vol. 7, Jul. 2008 (pp. 575-590).
Beggs et al., "P2X4R+ microglia drive neuropathic pain," Nature Neuroscience, vol. 15, No. 8, Aug. 2012 (pp. 1068-1073).
Ulmann et al., "Up-Regulation of P2X4 Receptors in Spinal Microglia after Peripheral Nerve Injury Mediates BDNF Release and Neuropathic Pain," The Journal of Neuroscience, Oct. 29, 2008, 28(44):11263-11268.
Chessell et al., "Distruption of the P2X7 purinoceptor gene abolishes chronic inflammatory and neuropathic pain," Pain 114 (2005) 386-396.

(Continued)

*Primary Examiner* — Amy L Clark
(74) *Attorney, Agent, or Firm* — Volpe Koenig

(57) ABSTRACT

The present invention is related to an active substance of *Hericium erinaceus* having a pain-relieving effect, and a pharmaceutical composition including the active substance. The active substance is prepared using the following steps: (a) inoculating a mycelium of *H. erinaceus* on an agar plate and incubating at 15-32° C. for 8-16 days; (b) inoculating the incubated *H. erinaceus* mycelia from step (a) into a medium in a flask and incubating at 20-30° C. and pH 4.5-6.5 for 3-5 days; (c) inoculating the incubated *H. erinaceus* mycelia from step (b) into a medium in a fermentation tank and incubating at 24-32° C. and pH 4.5-5.5 for 8-16 days to obtain a fermented medium of the *H. erinaceus* mycelia; and (d) desiccating the fermented medium of the *H. erinaceus* mycelia from step (c) to obtain the powder of the *H. erinaceus* mycelia, which is further purified and isolated to obtain a novel compound of *H. erinaceus*.

15 Claims, 11 Drawing Sheets

(56) References Cited

OTHER PUBLICATIONS

Honore et al., "A-740003 [N-(1-{[Cyanoimino)(5-quinolinylamino)methyl]amino}-2,2-dimethylpropyl)-2-(3,4-dimethoxyphenyl)acetamide], a Novel and Selective P2X7 Receptor Antagonist, Dose-Dependently Reduces Neuropathic Pain in the Rat," JPET 319:1376-1385, 2006.
Yang et al., "Cardiac P2X4 Receptors Targets in Ischemia and Heart Failure?" Circ Res. 2012; 111:397-401.
Drury et al., "The Physiological Activity of Adenine Compounds With Especial Reference To Their Action Upon The Mammalian Heart," J. Physiol. 1929, 68(3):213_237.
Burnstock, "Historical review: ATP as a neurotransmitter," Trends in Pharmacological Science, vol. 27, No. 3, Mar. 2006 (pp. 166-176).
Burnstock, "Purinergic P2 receptors as targets for novel analgesics," Pharmacology & Therapeutics 110 (2006) 433-454.
Burton et al., "Chronic Pain in the Cancer Survivor: A New Frontier," Pain Medicine, vol. 8, No. 2, 2007 (pp. 189-198).
Mao, "Chinese edible and pharmaceutical large fungi," Microbiology China, 1989,16(5):290-297.
Wang et al., "Antitumor And Immunoenhancing Activities Of Polysaccharide From Culture Broth of Hericium SPP.," Koahsiung J Med Sci 17:461-467, 2001.
Yang et al., "Hypolipidemic Effect of an Exo-biopolymer Produced from a Submerged Mycelial Culture of Hericium erinaceus," Biosci. Biotechnol. Biochem. 67(6), 1292-1298, 2003.
Saito et al., "Erinacine E as a Kappa Opioid Receptor Agonist and Its New Analogs from a Basidiomycete, Hericium ramosum," The Journal of Antibiotics, vol. 51, No. 11, Nov. 1998 (pp. 983-990).
Kenmoku et al., "Erinacine Q, a New Erinacine from Hericium erinaceus, and its Biosynthetic Route to Erinacine C in the Basidiomycete," Biosci. Biotechnol. Biochem. 66(3), 571-575, 2002.
Kenmoku et al., "Erinacol (Cyatha-3,12-dien-14beta-ol) and 11-O-Acetylcyathin A3, New Cyathane Metabolites from an Erinacine Q-Producing Hericium erinaceum," Biosci. Biotechnol. Biochem. 68(8), 1786-1789, 2004.
Watanabe et al., "Enantioselective Total Synthesis of (-)-Erinacine B," Organic Letters, 2007, vol. 9, No. 2, 359-362.
Watanabe et al., "Biomimetic Total Synthesis of (-)-Erinacine E," JACS 2008, 130, 1150-1151.
Lee et al., "Protective Effects of Hericium erinaceus Mycelium and Its Isolated Erinacine A against Ischemia-Injury-Induced Neuronal Cell Death via the Inhibition of iNOS/p38 MAPK and Nitrotyrosine," Int. J. Mol. Sci. 2014, 15, 15073-15089.
Li et al., "Evaluation of the toxicological safety of erinacine A-enriched Hericium erinaceus in a 28-day oral feeding study in Sprague-Dawley rats," Food and Chemical Toxicology 70 (2014) 61-67.
Nagai et al., "Dilinoleoyl-phosphatidylethanolamine from Hericium erinaceum protects against ER stress-dependent Neuro2a cell death via protein kinase C pathway," Journal of Nutritional Biochemistry 17 (2006) 525-530.
Jia et al., "Structural investigation of a novel rhamnoglucogalactan isolated from the fruiting bodies of the fungus Hericium erinaceus," Carbohydrate Research 339 (2004) 2667-2671.
Grynkiewicz et al., "A New Generation of $Ca^{2+}$ Indicators with Greatly Improved Fluorescence Properties," J. Bio. Chem. 1985, vol. 260, No. 6, Issue of Mar. 25, pp. 3440-3450.
Fukui et al., "Antinociceptive effects of intracerebroventricularly administered P2 purinoceptor agonists in the rat," European Journal of Pharmacology 419 (2001) 25-31.
Okada et al., "Analgesic Effects of Intrathecal Administration of P2Y Nucleotide Receptor Agonist UTP and UDP in Normal and Neuropathic Pain Model Rats," JPET 303:67-73, 2002.
Yaksh et al., "Microinjection of morphine into the periaqueductal gray evokes the release of serotonin from spinal cord," Brain Research 171 (1979) 176-181.
Kao et al., "Zinc Oxide Nanoparticles Interfere With Zinc Ion Homeostasis to Cause Cytotoxicity," Toxicological Sciences 125(2), 462-472 (2012).
Liu et al., "Comparative suppression of phthalate monoesters and phthalate diesters on calcium signalling coupled to nicotinic acetylcholine receptors," J. Toxicol. Sci., vol. 34, No. 3, 255-263, 2009.
Liu et al., "Muscarinic acetylcholine receptors present in human osteoblast and bone tissue," European Journal of Pharmacology 650 (2011) 34-40.
Burnstock, "Purinergic Signalling: Pathophysiology and Therapeutic Potential," Keio J Med 2013; 62(3):63-73.

\* cited by examiner

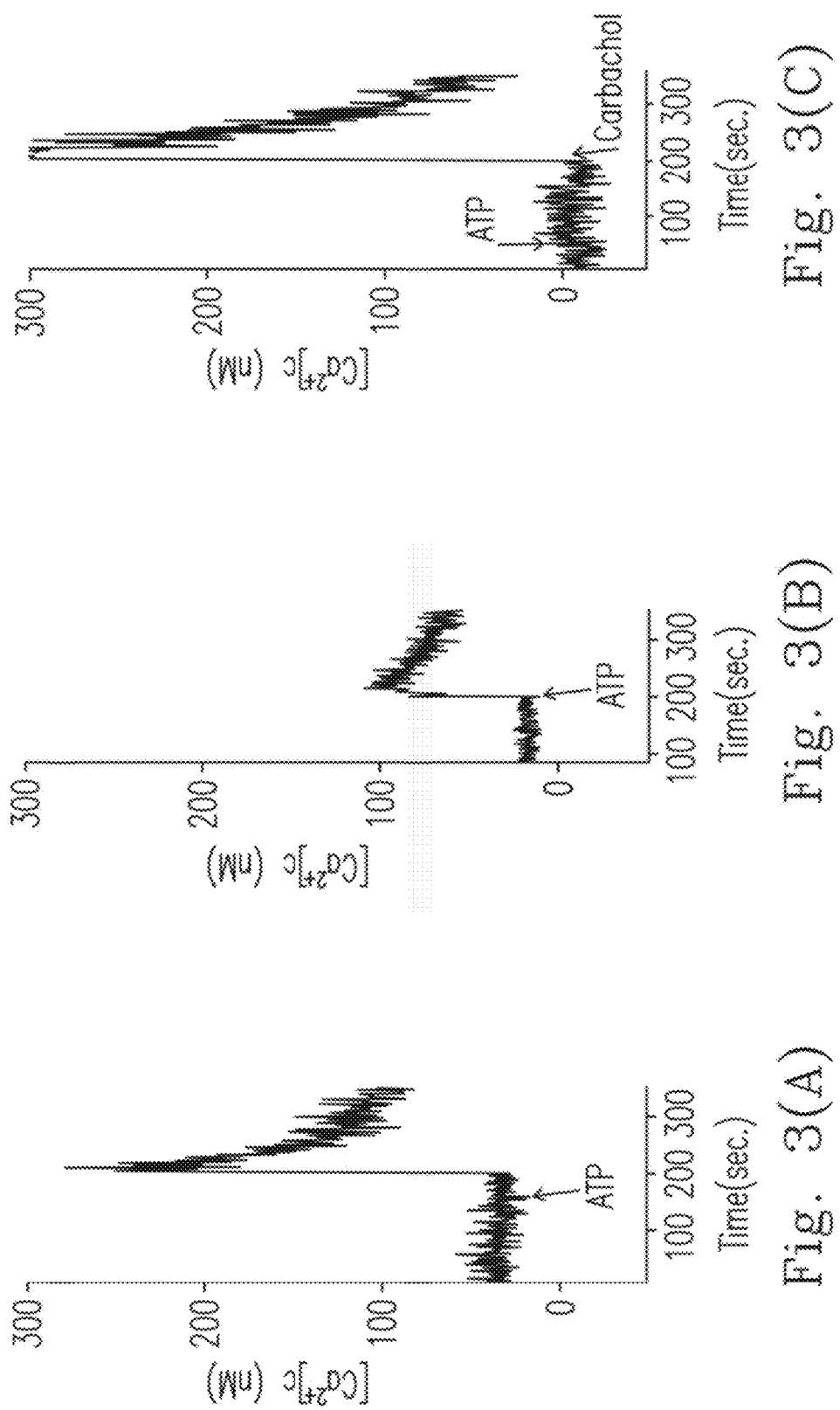

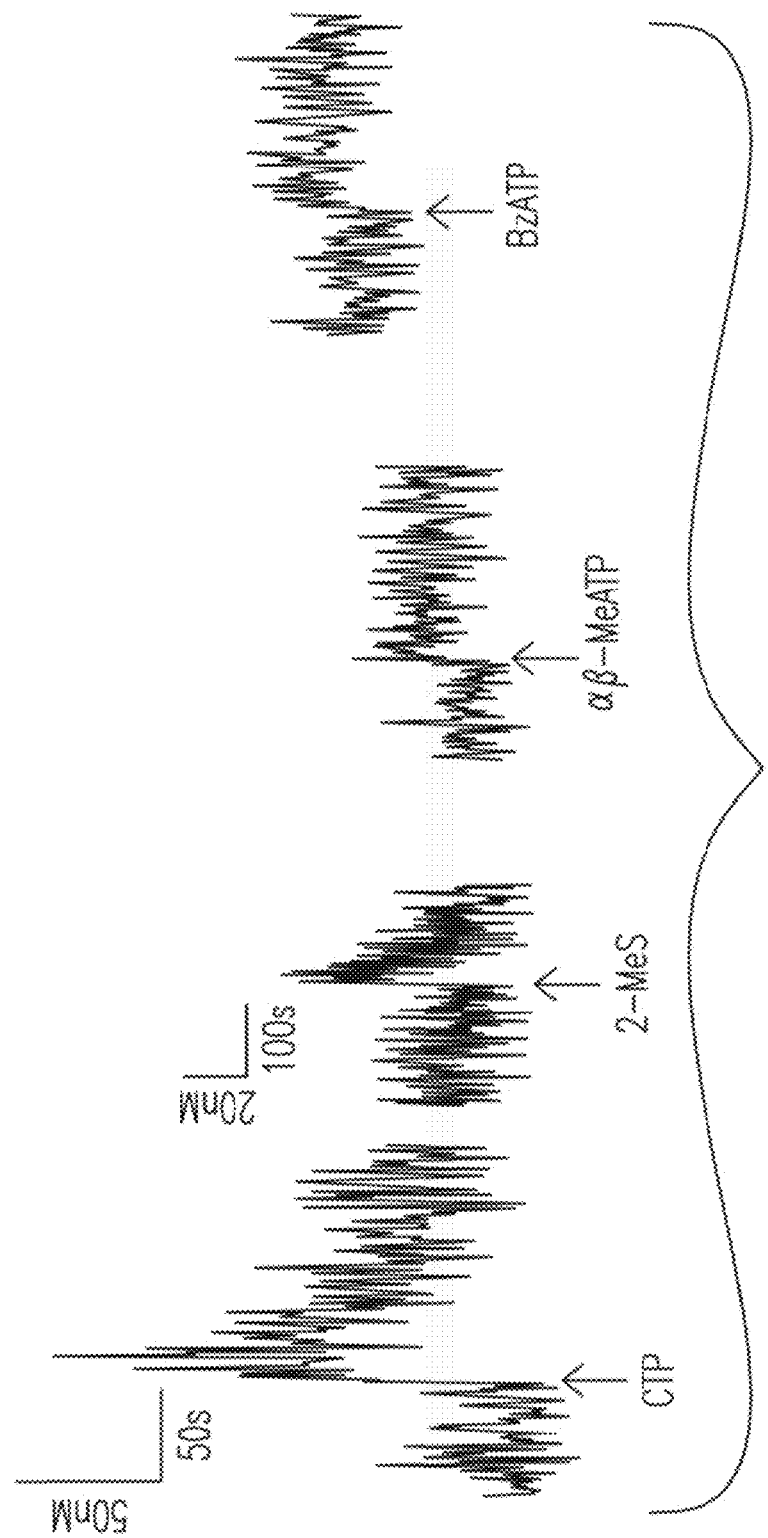

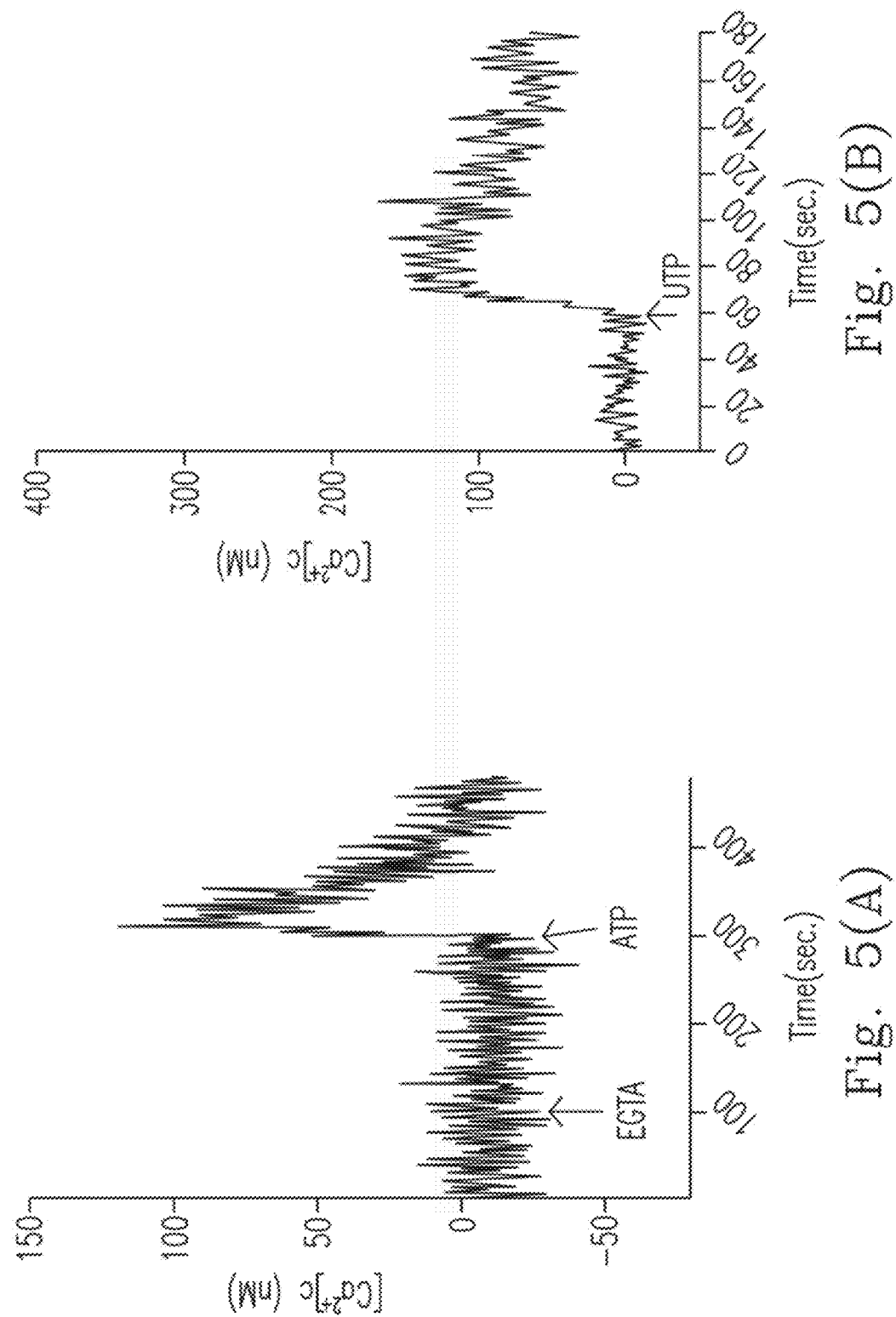

HERIPENES WITH PAIN-RELIEVING EFFECT, ACTIVE SUBSTANCES OF *HERICIUM ERINACEUS* MYCELIUM AND THE PREPARATION METHOD THEREOF, AND PHARMACEUTICAL COMPOSITION CONTAINING THE HERIPENES OR ACTIVE SUBSTANCES

CROSS REFERENCE TO RELATED APPLICATIONS

This application is a continuation of U.S. patent application Ser. No. 15/508,369, which is a 35 U.S.C. § 371 national stage application of PCT/CN2015/088813, which was filed Sep. 2, 2015, both of which are incorporated herein by reference as if fully set forth.

FIELD OF THE INVENTION

The present invention is related to an active substance with a pain-relieving effect, in particular, an active substance originated from *Hericium erinaceus*.

BACKGROUND OF THE INVENTION

The neural transduction pathway of nociception and the P2-purinoceptor (P2R)

The generation of nociception involves the transduction of pain signals on a series of neural pathways, finally arriving at the cerebrum, so that a human body feels pain. The neural transduction pathway of nociception starts from the generation of stimulation, followed by transforming this stimulation into neurosignals by nociceptors. The neurosignals are transmitted to the dorsal root ganglion (DRG), followed by transmission to the spinal cord and finally arrive at the nociception area in the thalamus of the cerebrum. In the preceding research, it is indicated that the distribution of the P2-purinoceptors (P2Rs) can be seen on a series of neural transduction pathways, e.g. the sensory nerves, the sympathetic nerves, the parasympathetic nerves and the central nervous system, wherein the P2Rs on the sensory nerves are mainly the $P2X_3$ receptor ($P2X_3R$) and the $P2X_{2/3}$ receptor ($P2X_{2/3}R$).

The literature with regard to the P2Rs and the neural transduction pathway of nociception is listed below.

1. The model of the gene knockout in mice proves that the $P2X_3R$, $P2X_4$ receptor ($P2X_4R$) and $P2X_7$ receptor ($P2X_7R$) are related to the nociceptor, pain transmission, inflammatory pain and neuropathic pain (Collier et al., Nature, 1966, 212(5060):411-412; Cockayne et at, Nature, 2000, 407 (6807):1011-1015; Souslova et al., Nature, 2000, 407(6807): 1015-1017; Jarvis and Burgard, Br. J. Pharmacol., 2002, 135(6):1343-1344; Tsuda et al., Nature, 2003, 424(6950): 778-783; Khakh and North, Nature, 2006, 442(7102):527-532; Burnstock, Nat. Rev. Drug Discov., 2008, 7(7):575-590; Beggs et at, Nat. Neurosci., 2012, 15(8):1068-1073).

2. The ATP of the $P2X_3R$ gene knockout mice does not induce the neural electrical signal transduction on the DRG, and does block the peripheral nociception which is transmitted to the central nervous system (Cockayne et al., Nature, 2000, 407(6807): 1011-1015).

3. The extent of the formalin-induced inflammatory pain is attenuated after deleting the $P2X_3R$ (Souslova et al., Nature, 2000, 407(6807):1015-1017).

4. The $P2X_3R$ antagonist can block the immediate pain, the inflammatory pain, and the visceral pain related to the neuropathic pain (Jarvis and Burgard, Br. J. Pharmacol., 2002, 135(6):1343-1344).

5. The expression of $P2X_4R$ increases sharply in the mice after a nerve injury, resulting in long-term pain-hypersensitivity (Tsuda et al., Nature, 2003, 424(6950):778-783).

6. It is found in the $P2X_4R$ knockout mice that the mice do not show the pain-hypersensitivity induced by the physical damage and lack the neural signaling pathways transmitted to the spinal cord because of a peripheral nerve injury (Ulmann et al., J. Neurosci. 2008. 28(44):11263-11268).

7. It is found that there is almost no inflammatory and neuropathic pain-hypersensitivity in the $P2X_7R$ knockout mice (Chessell et al., Pain, 2005, 114(3):386-396).

8. The $P2X_7R$ antagonist has the effect of reducing the neuropathic pain and the inflammatory pain (Honore, et al., J. Pharmacol. Exp. Ther., 2006, 319(3): 1376-1385).

P2R

P2R, based on its conformation and the signal transduction pathway, can be classified into two subfamilies, $P2X_1$-$P2X_7$ ($P2X_{1-7}$) receptors and $P2Y_1$-$P2Y_{14}$($P2Y_{1-14}$) receptors (Yang and Liang, Circ. Res., 2012, 111(4):397-401). Each of the $P2X_1$-$P2X_7$ receptors has two transmembrane domains, and its C- and N-terminal regions are within the cell. In addition, there is a loop-shaped protein structure outside the cell. Among the $P2X_1$-$P2X_7$ receptors, the smallest one, $P2X_4R$, has 388 amino acids, and the largest one, $P2X_7R$, has 595 amino acids. The P2X receptor (P2XR) is a cationic channel receptor, allowing $Na^+$ and $Ca^{2+}$ to pass through. After the P2X receptor is stimulated, $Ca^{2+}$ flows into the cells through the P2XR, so as to increase the intracellular free calcium-ion concentration ($[Ca^{2+}]c\uparrow$), which acts as a secondary signal to induce the subsequent physiological reactions. The neurosignals are sent to the thalamus of the cerebrum via the spinal cord to generate the nociception. At the same time, the increased intracellular free calcium-ion concentration ($[Ca^{2+}]c\uparrow$) further influences the cellular secretion. Concretely speaking, it may stimulate neuroimmunological cells to secrete cytokines. On the other hand, the $P2Y_{1-14}$ receptors are G-protein coupled receptors (GPCR). In addition to the $P2Y_{11-14}$ receptors, other P2Y subtypes are correlated to the G-protein (Gq). After actuation, Gq activates phospholipase C-β (PLC-β) to cleave the phosphatidylinositol 4,5-bisphosphate (PIP2) to generate inositol 1,4,5-trisphosphate (IP3). Next, the IP3 conjugates with the IP3 receptor on the endoplasmic reticulum (ER) of the cell, and calcium ions stored in the ER are released, resulting in the increased intracellular free calcium-ion concentration ($[Ca^{2+}]c\uparrow$). Accordingly, the P2XR and P2YR (except for the $P2Y_{11-14}$ receptors) can both use the variations of the intracellular free calcium-ion concentration as an index for monitoring the receptor functions.

Adenosine Triphosphate (ATP)

ATP is a well-known energy-carrying and energy-transferring biomolecule. Szent-Gyorgyi found in 1929 that the ATP also has extracellular biological functions (Drury and Szent-Györgyi, J. Physiol., 1929, 68(3):213-237). In 1996, ATP was formally deemed as a neurotransmitter in the neuroscience field. ATP acts as a neurotransmitter for P2R on the P2R-related neuronal signaling pathways. When the nerves are stimulated, ATP releases from the synaptic vesicles to the synaptic cleft and stimulates the P2R on the neuron behind the synapse. Subsequently, ATP is quickly decomposed by enzymes in the synaptic cleft. The neurotransmission model above is also supported by the published literature as in the following examples.

1. ATP mediates the signaling transmission at the presynaptic and the postsynaptic neurons, and plays a role in the neurotransmitter (Burnstock, Trends Pharmacol. Sci., 2006, 27(3):166-176; Burnstock, Nat. Rev. Drug Discov., 2008, 7(7):575-590).

2. ATP is released after tissue injury, and stimulates the P2R-mediated nociception on the pain receptor.

3. It is found that ATP may stimulate the P2R mediator on the human skin to induce the nociception (Collier et al., Nature, 1966, 212(5060): 411-412).

4. ATP plays an important role in the transmission of nociception (Burnstock, Pharmacol. Ther., 2006, 110(3): 433-454; Burnstock, Keio. J. Med., 2013, 62(3):63-73).

The Need for Analgesics

The analgesic market tends to become larger along with the aging population in society and gradual improvement to the requirements of quality of life. Among the various types of pain, the ones that are hard to treat are neuropathy-induced neuropathic pain and cancer pain. One reason is that there are few efficient drugs that thoroughly inhibit pain. Further, the relief of this long-term pain requires analgesics for long-term use. There are two main types of clinical analgesics, one is morphine analgesics, and the other is non-narcotic analgesics. If patients are administered with a morphine analgesic for a long time, this could cause tolerance and dependence problems. Tolerance means that the efficiency of a drug will gradually attenuate along with an increase of the given dosage, and it is necessary to increase the given dosage to achieve the analgesic effect. Non-narcotic analgesics do not have adverse reactions (such as respiratory depression, habituation and so on) similar to narcotics, but have analgesic and anti-inflammatory functions and can decrease the rising body temperature (antipyretic function) to attenuate the inflammatory symptoms. These drugs are usually used to relieve the mild-to-moderate pain caused by diseases such as rheumatism, arthritis, ischialgia, degenerative arthritis and so on. These drugs are also the nonsteroidal anti-inflammatory drugs (NSAIDs) with the side effects of the simultaneous inhibition of cyclooxygenase-1 (COX-1) and COX-2. When COX-2 is inhibited, the expression of prostaglandin I2 (PGI2) is decreased which results in the anti-inflammatory and analgesic functions and promotes the aggregation of blood platelets. When COX-1 is inhibited, the mucosal integrity of the gastrointestinal tract is destroyed and the renal blood flow is influenced. This results in side effects such as stomach injury, kidney injury and so on, and inhibits the platelet aggregation which results in frequent bleeding. Therefore, analgesics' safety, side effects, addiction and sensitivity to tolerance are all problems to be solved, so as to develop a more excellent analgesic agent.

*Hericium erinaceus*

The anesthesiologist Allen W. Burton stated, "New analgesics still cannot satisfy the demands of clinical oncology, and we frequently feel helpless to many intractable analgesic patients." (Burton et al., Pain Med., 2007, 8(2):189-198) Therefore, it is very important and urgently essential for the current clinical medicine to develop a safe and efficient analgesic against new biological pathways. Accordingly, starting from the consideration of safety, it is the current trend in industries to search for any active substances from natural edible materials and prepare the active substances as long-term drugs.

According to the description in *Medicinal Fungi of China*, "*H. erinaceus* tastes sweet, is neutral and tonic, has benefits for five viscera and digestion, and has excellent effects on dyspepsia, neurodegeneration, duodenal ulcer and gastric ulcer" (Mao, X.-L. Chinese edible and pharmaceutical large fungi. Microbiology China, 1989. 16(5):290-297). Therefore, it is known that *H. erinaceus*, a pharmaceutical and edible fungi, has an effect of disease treatment in ancient medicine. *H. erinaceus* is classified in the kingdom Fungi, the phylum Eumycota, the subphylum Basidiomycotina, the class Basidiomycetes, the order Aphyllophorales, the family Hydnaceae, the subfamily Hericioideae, and the genus *Hericium*. *H. erinaceus*'s fruiting body has a soft and spherical appearance with many bars with rough protuberances. *H. erinaceus* is white when fresh and turns tawny after being dried. The *H. erinaceus* fruiting body or mycelia extract contains saccharides (Wang et al., Kaohsiung J. Med. Sci., 2001, 17(9):461-467; Yang et al., Biosci. Biotechnol. Biochem., 2003, 67(6):1292-1298), erinacines (Saito et al., J. Antibiot., 1998, 51(11):983-990; Kenmoku et al., Biosci. Biotechnol. Biochem., 2002, 66(3):571-575; Kenmoku et al., Biosci. Biotechnol. Biochem., 2004, 68(8):1786-1789; Watanabe et al., Org. Lett., 2007, 9(2):359-362; Watanabe and Nakada, J. Am. Chem. Soc., 2008, 130(4):1150-1151; Lee et al., Int. J. Mol. Sci., 2014, 15(9):15073-15089; Li et al., Food Chem. Toxicol., 2014, 70:61-67), dilinoleoyl-phosphatidylethanolamine (DLPE) (Nagai et al., J. Nutr. Biochem., 2006, 17(8):525-530), amino acids, proteins, and minor elements (Jia et al., Carbohydr. Res., 2004, 339(16): 2667-2671). In the literature, it is common knowledge that polysaccharides of *H. erinaceus* have effects on immuno-regulation, blood lipid reduction, blood sugar reduction, the inhibition of gastric inflammation, or the occurrence of stomach cancer. So far, Japanese scientists have isolated and purified 14 erinacines, i.e. erinacines A, B, C, D, E, F, G, H, I, J, K, P, Q and R, from a submerged fermentation product. Erinacines can stimulate astrocytes in mice to secrete the neuron growth factors (NGF), so as to remedy diseases such as intellectual deterioration, neurodegeneration and so on. The inventors isolated, purified and identified novel compounds, i.e. heripenes, from the alcohol extract of the *H. erinaceus* mycelia, and proved in the experimental result that heripenes have the analgesia effect. The detail is described as follows.

SUMMARY OF THE INVENTION

The purpose of the present invention is to disclose the heripene and a preparation method for an active substance of *H. erinaceus*, and the preparation is used to prepare the heripene, the active substance and a pharmaceutical composition containing the heripene or the active substance for a pain-relieving effect.

To achieve this purpose, the present invention discloses a preparation method for an active substance of *H. erinaceus* having an effect of relieving a pain, including the following steps of:

(a) inoculating a mycelium of the *H. erinaceus* on an agar plate and incubating at a temperature of 15-32° C. for 8-16 days;

(b) inoculating the incubated mycelium of the *H. erinaceus* from step (a) into a medium in a flask and incubating at a temperature of 20-30° C. and pH 4.5-6.5 for 3-5 days;

(c) inoculating the incubated mycelium of the *H. erinaceus* from step (b) into a medium in a fermentation tank and incubating at a temperature of 24-32° C. and pH 4.5-5.5 for 8-16 days to obtain a fermented medium of the mycelium of the *H. erinaceus*; and (d) desiccating the fermented medium of the mycelium of the *H. erinaceus* from step (c) to obtain a powder of the mycelium of the *H. erinaceus*.

Preferably, an incubation in step (b) is a shaking incubation at a shaking rate of 100-250 rounds per minute (rpm).

Preferably, the fermentation tank in step (c) has a tank pressure of 0.8-1.2 kg/cm² and a stirring rate of 10-150 rpm, and a gas is introduced into the fermentation tank at an aeration rate of 0.5-1 volume per volume per minute (vvm).

Preferably, the gas is air, oxygen, carbon dioxide, nitrogen gas or a combination thereof.

Preferably, the medium used in step (b) and the medium used in step (c) are the same.

Preferably, the medium includes one or more combinations from a complex carbon and nitrogen source, animal or plant sources of protein or a hydrolyzate thereof, an inorganic salt, a saccharide, a yeast or a malt extract, and a defoaming agent.

Preferably, the complex carbon and nitrogen source is a grain or a legume, and the inorganic salt is a sulfate or a phosphate.

Preferably, the powder of the mycelium of the *H. erinaceus* from step (d) is further extracted with an alcohol solvent to obtain an alcohol extract of the mycelium of the *H. erinaceus*.

Preferably, the alcohol solvent is an ethanol of 30-100 volume-volume percentage (v/v %) or a methanol of 30-100 v/v %.

Preferably, the alcohol extract of the mycelium of the *H. erinaceus* is further extracted with a water and an ethyl acetate, followed by a column chromatography to obtain the heripene having a structural formula (I) as follows:

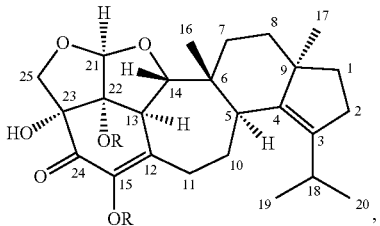

(I)

where R is hydrogen, hydroxyl, $C_1$-$C_{10}$ alkyl, $C_1$-$C_{10}$ alkenyl or $C_1$-$C_{10}$ alkynyl, which are optionally substituted with a substitute containing halogen, oxygen, nitrogen, phosphorus or sulfur; where the stereocenters at C-5, C-6, C-9, C-13, C-14, C-21, C22 and C-23 are an R-configuration or an S configuration.

The phrase "the functional group R being optionally substituted with a substituted" means that two functional groups R can be individually or both substituted with a substitute containing halogen, oxygen, nitrogen, phosphorus or sulfur.

Preferably, when the group R of the heripene having the structural formula (I) is hydrogen, the heripene is the erinacine S having a structural formula (II) as follows:

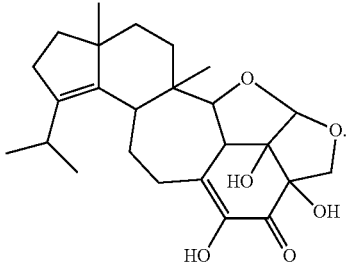

(II)

Preferably, a ratio of water to ethyl acetate is 1:4.

Preferably, the pain for treatment in the preparation method above is a neuropathic pain or a cancer pain.

Preferably, a signaling pathway for the pain in the preparation method above includes a P2-purinoceptor (P2R).

The present invention further discloses an active substance of the *H. erinaceus* having an effect of reducing a pain and being prepared by any one of the preparation methods above.

Preferably, the active substance of the *H. erinaceus* is powder after being prepared by the preparation method above.

Preferably, the active substance of the *H. erinaceus* is an alcohol extract after being prepared by the preparation method above.

Preferably, the active substance of the *H. erinaceus* is the heripene having a structural formula (I) after being prepared by the preparation method above.

Preferably, the heripene is the erinacine S having the structural formula (II) when R of the heripene of the structural formula (I) is hydrogen.

The present invention further discloses a heripene compound having a structural formula (I).

Preferably, the heripene compound is the erinacine S having a structural formula (II) when R of the heripene compound of the structural formula (I) is hydrogen.

Preferably, the heripene compound above has a pain-relieving effect.

The present invention further discloses a pharmaceutical composition having a pain-relieving effect, including an active substance of the *H. erinaceus* above, and a biologically acceptable carrier, excipient, diluent or adjuvant.

The present invention further discloses a pharmaceutical composition having a pain-relieving effect, including a heripene compound above, and a biologically acceptable carrier, excipient, diluent or adjuvant.

BRIEF DESCRIPTION OF THE DRAWINGS

FIGS. 3(A), 3(B) and 3(C) show the calcium signals of the receptor in the cells, which are monitored after cells are filled with a fluorescent agent according to Item 1 of Embodiment 6, wherein (A) human osteosarcoma HOS cells, (B) rat pheochromocytoma PC12 cells, and (C) human neuroblastoma SH-SY5Y cells are stimulated with ATP and then with carbachol.

FIG. 4 shows the calcium signals correlated with the P2XR subtypes in human osteosarcoma HOS cells according to Item 2 in Embodiment 2.

FIGS. 5(A) and 5(B) show the calcium signals correlated with the P2YR subtypes in human osteosarcoma HOS cells according to Item 2 in Embodiment 2, wherein (A) the calcium signals are induced by ATP stimulation in a calcium free buffer, and (B) the calcium signals are induced by uridine triphosphate (UTP) stimulation.

the erinacine S treatments, followed by the ATP stimulation in the human osteosarcoma HOS cells according to Item 4 in Embodiment 6.

Figure 8:
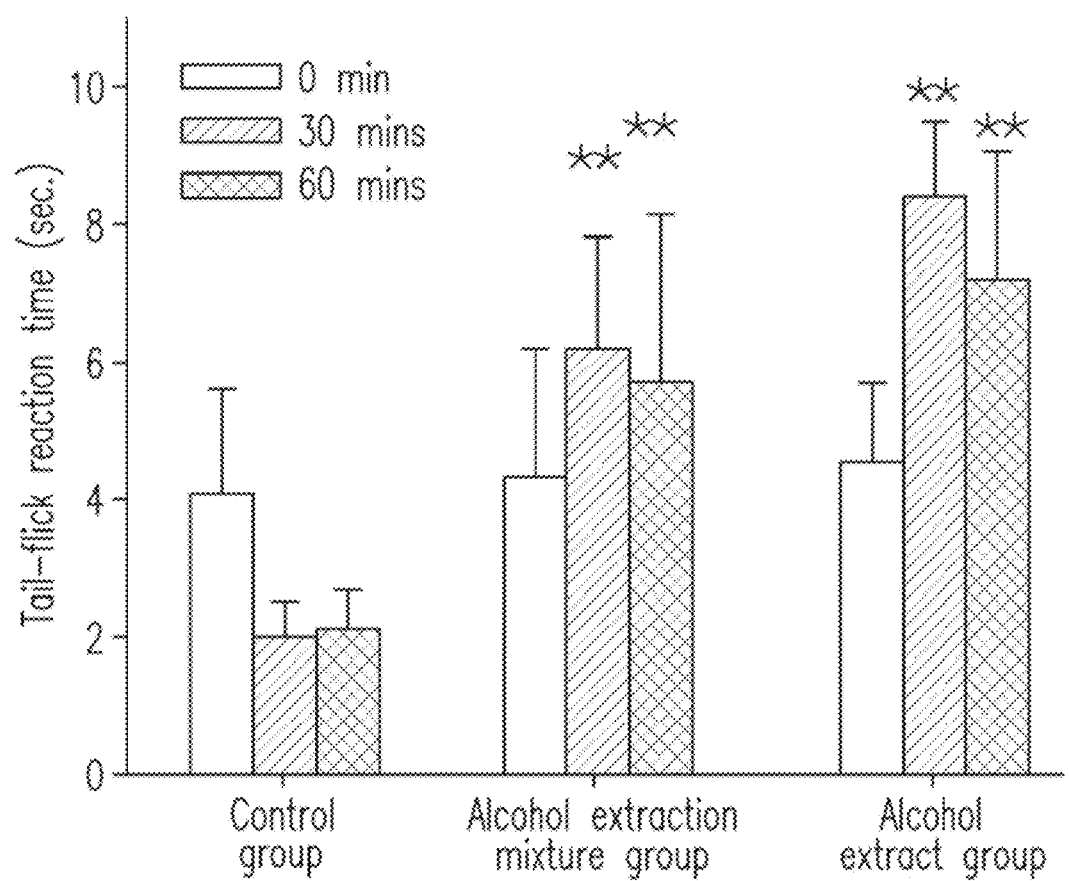

FIG. 8 shows the comparisons between groups in the tail-flick test on delaying the short-term pain-relieving effect after administering the *H. erinaceus* alcohol extraction mixture or alcohol extract according to Item 1 in Embodiment 7.

Figure 9:
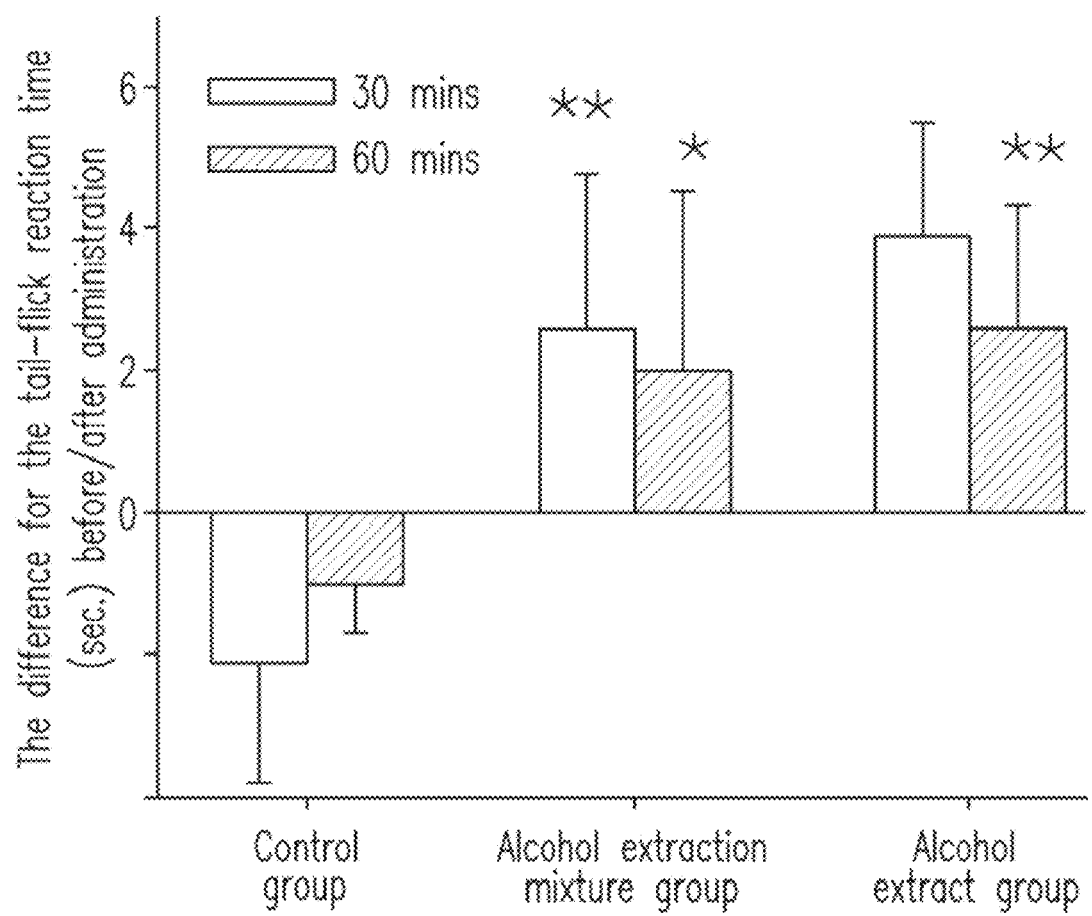

FIG. 9 shows the comparisons between groups in the tail-flick test on delaying the short-term pain-relieving effect before/after administering the *H. erinaceus* alcohol extraction mixture or alcohol extract according to Item 2 in Embodiment 7.

Figure 10:
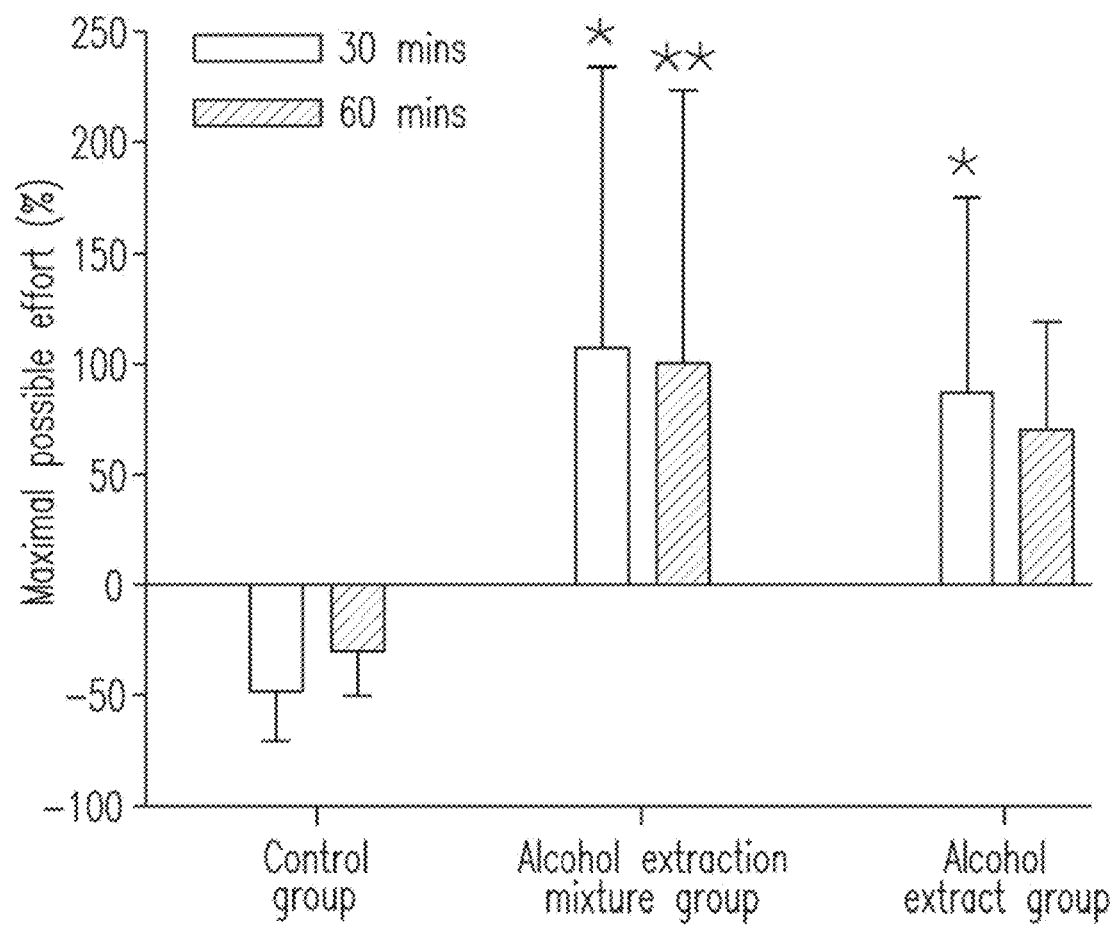

FIG. 10 shows the comparisons of the maximum possible effect calculated from the differences in the tail-flick test on delaying the short-term pain-relieving effect before/after administering the *H. erinaceus* alcohol extraction mixture or alcohol extract according to Item 3 in Embodiment 7.

Figure 11:
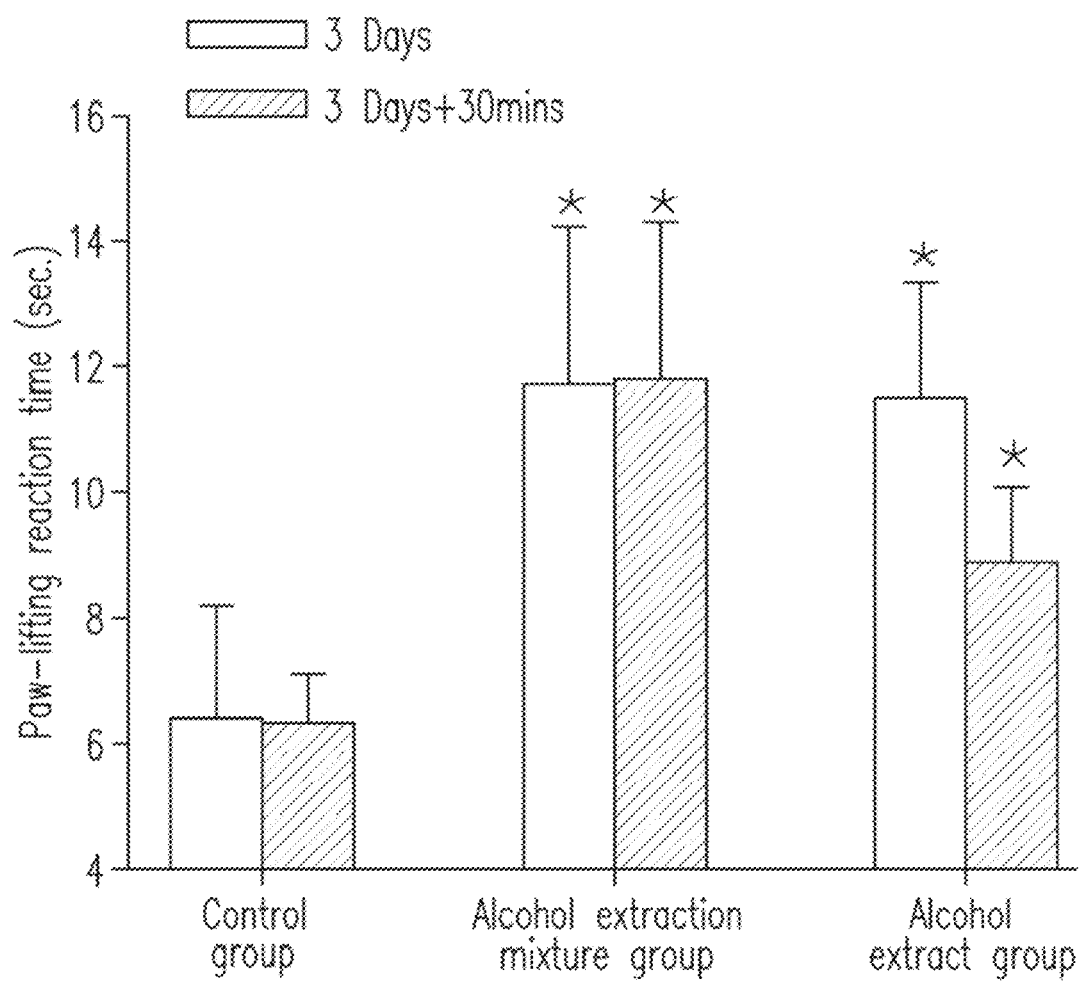

FIG. 11 shows the comparisons between groups in the hot-plate test on delaying the long-term pain-relieving effect after administering the *H. erinaceus* alcohol extraction mixture or alcohol extract according to Item 4 in Embodiment 7.

DETAILED DESCRIPTION OF THE PREFERRED EMBODIMENTS

The purpose of the present invention is to provide a preparation method to prepare the miscellaneous types of active substances from *H. erinaceus*. Furthermore, novel heripene compounds are isolated and purified, and the heripenes and the active substances can further be prepared as a pharmaceutical composition with the pain-relieving effect.

Principles of the Experiments

The cellular model for P2R is established to detect the P2R's functions. At first, the P2R expression in the cell line is detected by the reverse transcription-polymerase chain reaction (RT-PCR). The receptor's functions are detected by the stimulation of the stimulator. The intracellular free calcium-ion concentration is used as the detection target of the receptor's functions because P2XR and P2YR can both be correlated with calcium-ion signaling. Although nociception can be generated in the central nervous system by the P2R transmission, it still needs to be confirmed via animal behavior. The pain-relieving effect of the active substances in the present invention can be identified by determining the generation of pain. Therefore, the level of nociception in live animals is determined by two behavioral experiments, the tail flick test and the hot-plate test. In the present invention, the potential analgesic active components are prepared from the naturally edible mushroom, analyzed via the nociception mechanism and the experiments on animals' behavior, and further prepared as a pharmaceutical composition including the erinacine S or the active substances.

EXPERIMENTAL METHOD

The Source of the Species:

The species, *Hericium erinaceus*, used in the embodiments of the present invention has been deposited in the China General Microbiological Culture Collection Center (CGMCC), Beijing, China with the Deposit No. CGMCC 10905. Originally, this species was purchased from the Bioresource Collection and Research Center (BCRC) of the Food Industry Research and Development Institute, Taiwan, with the Accession No. BCRC 35669. However, the active substances of *H. erinaceus* described in the present invention are not limited to one from which this species is obtained.

Submerged Cultivation:

The liquid culture of the *H. erinaceus* mycelia is described as follows. The mycelium of *H. erinaceus* was inoculated on an agar plate to incubate at an adequate temperature of 15-32° C. for about 14 days. Subsequently, the mycelium was inoculated into a medium (where the ingredients are listed below) in a flask, and incubated to the early log phase with shakes at 20-30° C., pH 4.5-6.5 at the shaking rate of 100-250 rounds per minute (rpm) for 3-5 days. Finally, the culture in the flask was inoculated into the medium (which has the same ingredients as in the flask) of the fermentation tank, and cultured at 24-32° C., a tank pressure of 0.8-1.2 $kg/cm^2$, a pH value of about 4.5-5.5, an aeration rate of a gas of 0.5-1 volume per volume per minute (vvm) and a stirring rate of 10-150 rpm for 8-16 days to obtain a fermentation medium of *H. erinaceus* mycelia including the mycelia and the supernatant, where the gas is air, a mixture of air, oxygen, carbon dioxide or nitrogen, and the preferred gas is air.

The formula of the medium is listed as follows.

| Ingredients | Amount (wt. %) |
| --- | --- |
| Complex carbon and nitrogen source | 0.01-10 |
| Animal or plant sources of protein or its hydrolyzate | 0.01-5 |
| Yeast or melt extract thereof (powder or cream) | 0.001-2 |
| Inorganic salt | 0.0001-2 |
| Saccharide | 0.01-20 |
| Defoaming agent | 0.01-0.5 |
| Water | Add to 100 wt. % |

The complex carbon and nitrogen source may be grain (e.g. wheat powder or wheat bran) or legume (e.g. soybean flour, mung bean flour and so on), the inorganic salt may be magnesium sulfate, potassium hydrogen phosphate, potassium dihydrogen phosphate, ferric sulfate, zinc sulfate and so on, the saccharide may be glucose, fructose, maltose, sucrose and so on, and the remainder is water in addition to the ingredients above.

A defoaming agent may be additionally supplemented into the medium in the fermentation tank to prevent the generation of too much foam during the cultivation, and may be commercially common ones, such as a 0.01% water-based defoaming agent including silicon oil and silicones. The cultivation method in the embodiment is described below in detail.

The detection of calcium signals using fluorescence:

Cells were filled with a fluorescent dye-based calcium indicator, "Fura-2, AM cell permeant" (ThermoFisher Scientific, Waltham, Mass., U.S.A.), and the variation of the fluorescence level at an emission wavelength of 505 nm was determined at two excitation wavelengths of 340 nm and 380 nm using a fluorescence spectrometer (SPEX® 1681, Spec Industries, Inc., New Jersey, U.S.A.). During the experiment, ATP was added to cells to stimulate the P2R expression, and the variation of the fluorescence level was observed. Finally, 1 wt. % digitonin was added to enable the cells to become transparent, and the maximum fluorescence ratio (Rmax) was obtained at a concentration of 2 mM $Ca^{2+}$. Ethyleneglycol bis(2-aminoethylether)tetraacetic acid (EGTA) then was added to chelate with the calcium ions to obtain a minimum fluorescence ratio (Rmin). The dissociation coefficient (Kd) of fura-2 to $Ca^{2+}$ is 225 nM. The intracellular calcium-ion concentration was calculated using formulas (Grynkiewicz et al., J. Biol. Chem. 1985. 260(6): 3440-3450).

Tail Flick Test:

The tail flick test (also called the thermosensitive tail-flicking assay) (Fukui et a., Eur. J. Pharmacol. 2001. 419 (1):25-31; Okada et al., J. Pharmacol. Exp. Ther. 2002. 303(1):66-73) is mainly used to measure the threshold of nociception when a mouse's tail is stimulated by infrared radiation. During the experiment, mice were not anesthetized, and the mouse tail (1 to 2 cm away from the end) was disposed on a specific groove of a heating panel. Next, the infrared radiation heater from an infrared light source calibrator was turned on, and the emitted infrared concentrated on the mouse tail via a paraboloid reflector. When the experimental animal felt pain, its tail gently flicked the panel, and thus this reaction is called the tail flick test. When the tail flick reaction occurred, the built-in sensor detected this reaction and recorded the tail-flick reaction time. The threshold of nociception may be expressed as the seconds of the tail flick, also may be expressed as the variation of seconds before/after administration. Even the variation of the seconds of tail flick can be further calculated as a maximum possible effect (MPE). The formula is: (% MPE) =(Postdrug latency−Predrug latency)/(Cutoff time−Predrug latency)×100%.

Hot-Plate Test:

In the mouse hot-plate test (Yaksh and Tyce, Brain Res. 1979. 171(1):176-181), the heater was first pre-heated to a specific temperature, and then the experimental animal was subjected to the heat stimulation from the metal plate of the heater. The reaction that the experimental animal felt pain and jumped due to heat is called the paw withdrawal reaction. The required time that each experimental animal jumps after being disposed on the heater is called the paw withdrawal reaction time. Finally, the paw withdrawal reaction time refers to the threshold of nociception for the experimental animal.

Embodiment 1: The Incubation of *H. erinaceus* Mycelium and the Preparation of its Active Substances The incubation on the agar plate:

The *H. erinaceus* mycelium was inoculated on a potato dextrose agar (PDA) plate and incubated at 25° C. for about 7 days.

The incubation in the flask:

The *H. erinaceus* mycelium was aseptically scraped from the agar plate above to inoculate into the medium (see below) in the flask, followed by the shaking incubation in the orbital incubator at a shaking rate of 120 rounds per minute (rpm), at about 26° C., pH 5.0 for 5 days.

The formula of the medium is listed as follows.

| Ingredients | Amount (wt. %) |
| --- | --- |
| Glucose | 2.0 |
| Yeast extract | 0.1 |
| Animal or plant sources of protein and its hydrolyzate | 0.1 |
| Magnesium sulfate | 0.001 |
| soybean flour | 0.1 |
| Water | Add to 100 wt. % |

The incubation in the fermentation tank:

The medium used in the fermentation tank is the same as the incubation step for the flask. The incubated mycelia in the flask were inoculated into the medium in the fermentation tank. At 26° C., a tank pressure of 0.5-1.0 kg/cm$^2$, pH 5.0 and with or without (air lift) a stirring rate of 10-150 rpm, air was introduced at an aeration rate of 0.5-1 volume per volume per minute (vvm), and the inoculated mycelia were incubated for 12 days. The fermented medium containing the mycelia, the supernatant and the active substances having the pain-relieving effect was obtained after 12 days. The fermented medium was freeze-dried to obtain freeze-dried powder of the *H. erinaceus* mycelia (abbreviated as "the freeze-dried powder"). A 20-metric ton fermented medium was freeze-dried to obtain about 80 kg freeze-dried powder.

Embodiment 2: The Alcohol Extraction of the Active Substances of *H. erinaceus* Mycelia The freeze-dried powder of the *H. erinaceus* mycelia was added to a 95 v/v % ethanol solution (1:25 w/w) to perform a first extraction, followed by the ultra-sonication at a sonication rate of 120 rpm for 1 hour. The suspension was centrifuged to obtain the supernatant. A second extraction was performed on the supernatant using 85 v/v % ethanol solution, and the ultra-sonication and centrifugation steps above were repeated to obtain a supernatant. Finally, the supernatant was concentrated under reduced pressure to obtain a cream of the *H. erinaceus* mycelia alcohol extract (hereinafter abbreviated as "the alcohol extract").

Embodiment 3: The Preparation of the Alcohol Extract Mixture

The freeze-dried powder and an equal amount of the alcohol extract were mixed, and then centrifuged to obtain the supernatant. The supernatant was freeze-dried to obtain a mixture of the *H. erinaceus* mycelia and the alcohol extract (hereinafter abbreviated as "the alcohol extraction mixture").

Embodiment 4: The Preparation and Analysis of the Erinacine S Standard

Figure 1:
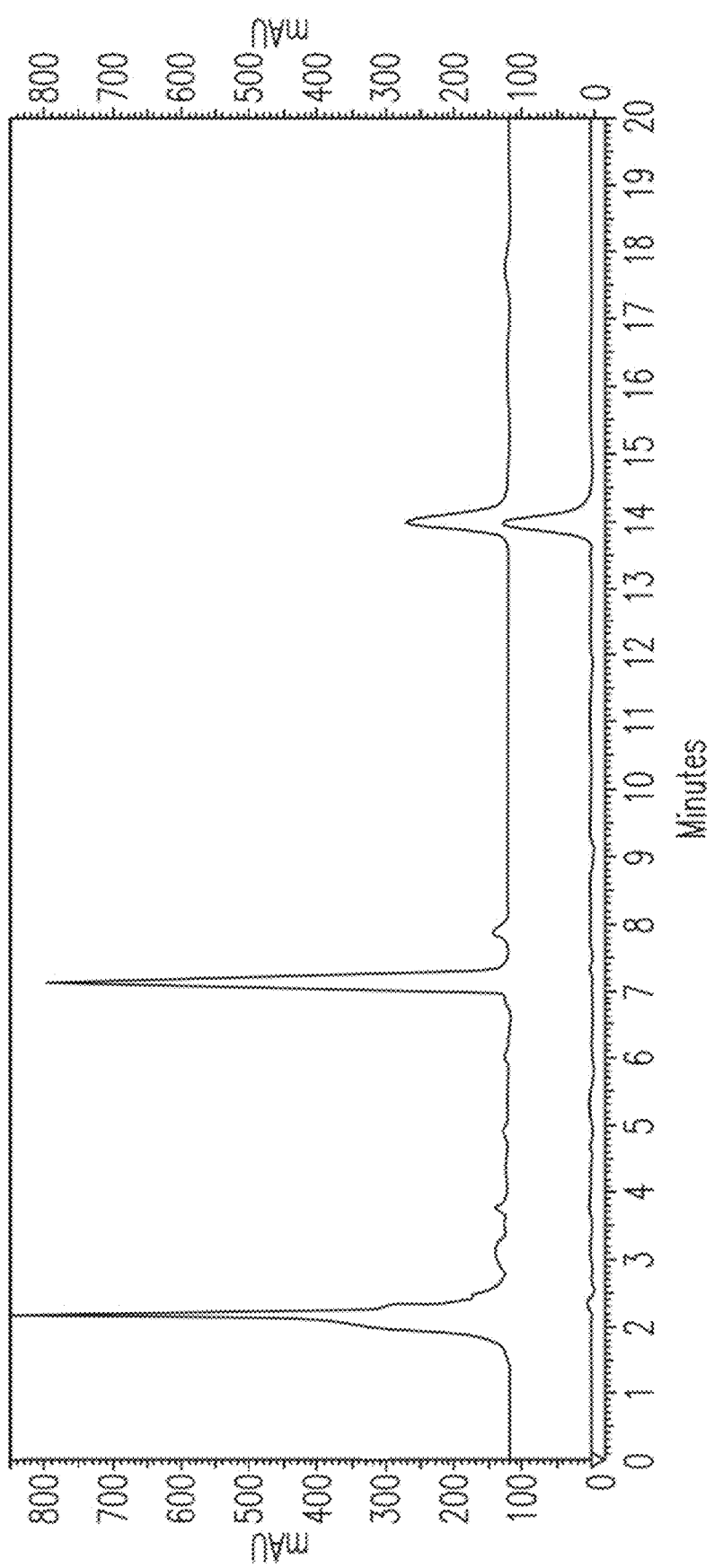
FIG. 1 illustrates an HPLC analytic spectrum of the erinacine S according to Embodiment 4.

The preparation method for the erinacine S standard is described as follows. The *H. erinaceus* mycelia alcohol extract was subjected to liquid-liquid partition (H$_2$O:ethyl acetate (EA)=1:4 (v/v)), and the obtained ethyl acetate extract was further subjected to column chromatography on silica gel and Sephadex® LH-20 silica gel, followed by the gradient elution of n-hexane:EA (10:1, 3:1, 3:2, 1:1, 1:2, 0:1; v/v), to obtain 7 sub-partitions. The sub-partition 3 (which was eluted with n-hexane:EA=3:2 (v/v)) was further subjected to column chromatography on the Sephadex LH-20 silica gel to obtain a new compound, erinacine S (i.e. formula (I)), whose structural formula was identified via chemical analysis, and characteristic analysis was performed via high performance liquid chromatography (HPLC). The erinacine S was obtained using a reverse chromatography column Cosmosil 5C18-AR-II (Nacalai USA, California, U.S.A.) at 40° C. and eluted using acetonitrile starting from 60 volume % and reaching to 65 volume % within 20 minutes at 1 ml/min of flow rate and 290 nm of the UV detection wavelength. The retention time of the erinacine S is 14 minutes. The HPLC analytic result is shown in FIG. 1 (where the label is the erinacine S standard). In FIG. 1, the upper curve indicates the freeze-dried powder of the *H. erinaceus* mycelia alcohol extract, and the lower curve indicates the erinacine S standard. The erinacine S standard is a standard prepared using the method above by the Applicant, and acts as a quantification basis for the erinacine S in the components of the extract.

The chromatography plot of the prepared alcohol extract in Embodiment 2 shows that peaks appear at the retention times of 2, 7 and 14 minutes. Comparing the erinacine S standard with the one peak at 14 minutes, it can be determined that the peak indicates erinacine S. The erinacine S in the alcohol extract is quantified as 59 ppm.

The $^1$H and $^{12}$C nuclear magnetic resonance (NMR) of the erinacine S are described in the following table.

| position | $\delta_H$ (multiplicity, J in Hz) | $\delta_C$ | HMBC (H→C) |
|---|---|---|---|
| 1 | 1.54 (1H, dt, 13.2, 7.8) | 38.2 (t) | C2, C-3, C-4, C-8, C-9, C-17 |
|   | 1.61 (1H, dt, 13.2, 7.8) |   |   |
| 2 | 2.28 (2H, t, 7.2) | 28.4 (t) | C-1, C-3, C-4, C-9 |
| 3 |   | 138.6 (s) |   |
| 4 |   | 139.3 (s) |   |
| 5 | 2.64 (1H, d, 9.6) | 46.5 (d) | C-3, C-4, C-6, C-9, C-10, C-11, C-16 |
| 6 |   | 42.5 (s) |   |
| 7 | 1.80 (2H, m) | 28.9 (t) | C-5, C-6, C-8, C-9, C-16 |
| 8 | 1.40 (1H, m) | 36.8 (t) | C-1, C-7, C-9, C-17 |
|   | 1.51 (1H, dd, 12.6, 6.0) |   |   |
| 9 |   | 49.6 (s) |   |
| 10 | 1.69 (1H, m) | 25.1 (t) | C-4, C-5, C-6, C-11, C-12 |
|   | 2.02 (1H, m) |   |   |
| 11 | 1.99 (1H, m) | 32.3 (t) | C-12, C-13, C-15 |
|   | 3.76 (1H, m) |   |   |
| 12 |   | 129.4 (s) |   |
| 13 | 3.80 (1H, dd, 10.8, 1.8) | 49.1 (d) | C-6, C-12, C-14, C-15, C-22, C-23 |
| 14 | 4.40 (1H, d, 10.8) | 91.3 (d) | C-6, C-7, C-12, C-16 |
| 15 |   | 142.7 (s) |   |
| 16 | 1.11 (3H, s) | 19.4 (q) | C-5, C-6, C-7, C-14 |
| 17 | 1.07 (3H, s) | 25.0 (q) | C-1, C-4, C-8, C-9 |
| 18 | 2.77 (1H, septet, 6.6) | 27.3 (d) | C-2, C-3, C-4, C-19, C-20 |
| 19 | 0.97 (3H, d, 6.6) | 21.4 (q) | C-3, C-18, C-20 |
| 20 | 0.98 (3H, d, 6.6) | 21.9 (q) | C-3, C-18, C-19 |
| 21 | 6.13 (1H, s) | 113.3 (s) | C-13, C-14, C-25 |
| 22 |   | 93.0 (s) |   |
| 23 |   | 83.2 (s) |   |
| 24 |   | 193.6 (s) |   |
| 25 | 4.48 (1H, d, 10.2) | 80.8 (t) | C-21, C-22, C-23, C-24 |
|   | 4.60 (1H, d, 10.2) |   |   |
| 15-OH | 10.76 (1H, s) |   | C-12, C-15, C-24 |

Embodiment 5: The Establishment and Analysis of the Cell Model for P2R

1. The Incubation of Cells:

Three cell lines, i.e. rat pheochromocytoma cell line PC12, human neuroblastoma cell line SH-SY5Y and human osteosarcoma cell line HOS, were used. PC12 cells were incubated in a Dulbecco's Modified Eagle Medium (DMEM) supplemented with 10% (v/v) horse serum (HS) and 5% (v/v) fetal bovine serum (FBS) (Kao et al., Toxicol. Sci., 2012, 125(2):462-472). Human neuroblastoma SH-SY5Y cells were incubated in a DMEM/F-12 medium supplemented with 10% (v/v) FBS (Liu et al., J. Toxicol. Sci., 2009, 34(3):255-263). HOS cells were incubated in a minimum essential medium (MEM) (containing Earle's salts, 2 mM L-glutamine and 0.1 mM non-essential amino acids) supplemented with 1.5 g/L sodium bicarbonate and 1 mM pyruvate sodium, and an extra 5% (v/v) FBS was added during use. Cells were grown in a 5% $CO_2$ humidified incubator at 37° C. The medium was replaced every 2-3 days, and cells were sub-cultured using trypsin-ethylenediaminetetraacetic acid (EDTA) (Liu et al., Eur. J. Pharmacol., 2011, 650(1):34-40).

2. The Detection of P2R mRNA:

Messenger RNA (mRNA) was extracted from cells to prepare complementary DNA (cDNA). Specific primers for individual P2R subtype receptors were designed, wherein SEQ ID NOs: 1~2, 3~4, 5~6, 7~8, 9~10, 11~12 and 13~14 respectively are primers for human $P2X_1$, $P2X_2$, $P2X_3$, $P2X_4$, $P2X_5$, $P2X_6$ and $P2X_7$ subtype receptors, SEQ ID NOs: 15~16, 17~18, 192~0, 21~22, 23~24, 25~26, 27~28 and 29~30 respectively are primers for human $P2Y_1$, $P2Y_2$, $P2Y_4$, $P2Y_5$, $P2Y_6$, $P2Y_9$, $P2Y_{10}$ and $P2Y_{11}$ subtype receptors, SEQ ID NOs: 31~32 are primers for human β-actin, SEQ ID NOs: 33~34, 35~36, 37~38, 39~40, 41~42, 43~44 and 45~46 respectively are primers for rat $P2X_1$, $P2X_2$, $P2X_3$, $P2X_4$, $P2X_5$, $P2X_6$ and $P2X_7$ subtype receptors, SEQ ID NOs: 47~48, 49~50, 51~52, 53~54, 55~56, 57~58 and 59~60 respectively are primers for rat $P2Y_1$, $P2Y_2$, $P2Y_4$, $P2Y_6$, $P2Y_{12}$, $P2Y_{13}$ and $P2Y_{14}$ subtype receptors, and SEQ ID NOs: 61~62 are primers for rat glyceraldehyde-3-phosphate dehydrogenase (GAPDH), and the mRNA expressions of the P2R subtype receptors were amplified using polymerase chain reaction (PCR) and monitored. At first, cells were washed with phosphate buffered saline (PBS), and mRNA was obtained in the column using a NucleoSpin® RNA II kit (MACHEREY-NAGEL GmbH & Co. KG, Duren, Germany), and the concentration of RNA was determined using an ACTGene ASP-2680 spectrophotometer (CellTAGen, Seoul, Republic of Korea). Furthermore, the reverse transcriptase-polymerase chain reaction (RT-PCR) was performed using SuperScript® III Reverse Transcriptase (Invitrogen™, ThermoFisher Scientific, Waltham, Mass., U.S.A.). mRNA was reverse-transcribed as cDNA, and then PCR was performed on this cDNA using a Q-Amp™ 2× HotStart PCR master mix (containing Taq DNA polymerase) (Bio-Genesis Technologies, Inc., Taiwan) and the P2R primers. The obtained PCR product was electrophoresed in 1.5% (w/v) agarose gel in the buffer (containing 0.5× Tris-borate EDTA (TBE)) in an electrophoresis tank. The voltage during the electrophoresis was set at 50 V, and the voltage was increased to 100 V for 15 minutes. After electrophoresis, the agarose gel was stained with ethidium bromide (EtBr), and then was transferred to a gel image system to be illuminated by ultraviolet (UV) radiation. The gel image was recorded, and the P2R expressed by the cells was observed.

Figures 2A, 2B:
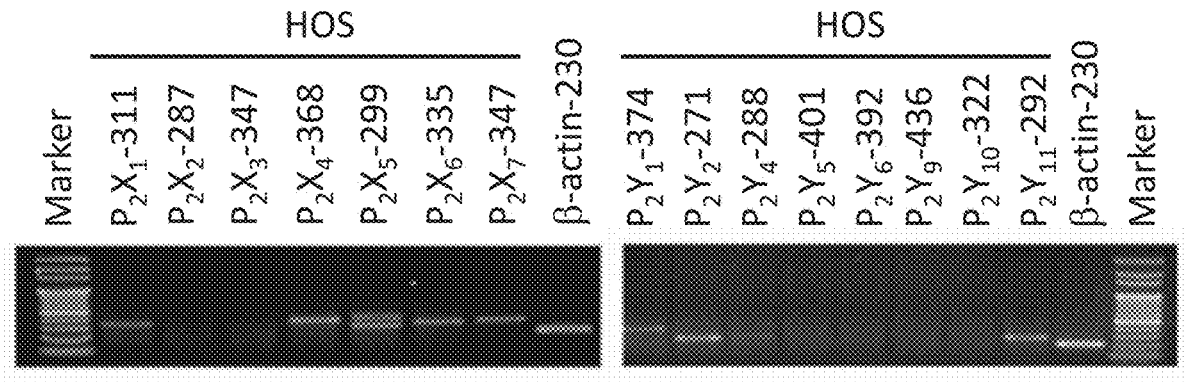
FIGS. 2(A), 2(B), 2(C), 2(D), 2(E) and 2(F) show the gene expression of the P2R receptors in the cells, which are monitored using the RT-PCR according to Item 2 of Embodiment 5.
Figures 2C, 2D:
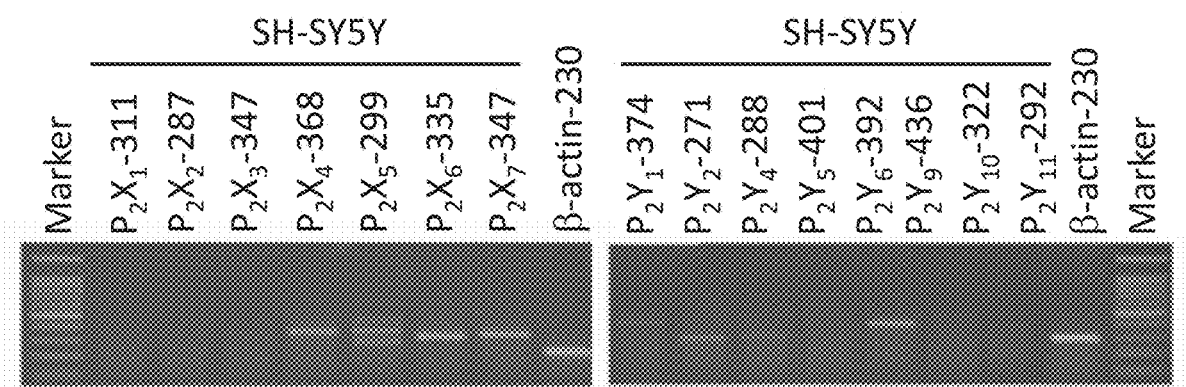
Figures 2E, 2F:
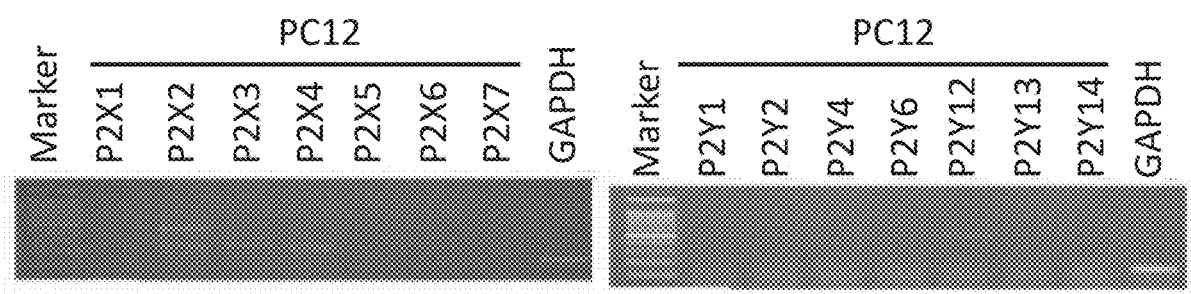

The gene expressions of P2R in the rat pheochromocytoma cell line PC12, human neuroblastoma cell line SH-SY5Y and human osteosarcoma cell line HOS were determined using RT-PCR. FIGS. 2(A), 2(C) and 2(E) show the mRNA expressions of the P2X subtype receptors, FIGS. 2(B), 2(D) and 2(F) show the mRNA expressions of the P2Y subtype receptors, and HOS, SH-SY5Y or PC12 in the lower left corner in each panel is the cell line's name. It can be seen that the P2XR subtypes (i.e. $P2X_1R$, $P2X_4R$, $P2X_5R$, $P2X_6R$ and $P2X_7R$) and the P2YR subtypes (i.e. $P2Y_1R$, $P2Y_2R$, $P2Y_4R$, $P2Y_6R$ and $P2Y_{11}R$) were detected in the human osteosarcoma cell line HOS, the P2XR subtypes (i.e. $P2X_3R$, $P2X_4R$, $P2X_5R$, $P2X_6R$ and $P2X_7R$) and the P2YR subtypes (i.e. $P2Y_1R$, $P2Y_2R$, $P2Y_4R$ and $P2Y_{11}R$) were detected in the human neuroblastoma cell line SH-SY5Y, and the P2XR subtypes (i.e. $P2X_2R$, $P2X_3R$ and $P2X_4R$) and the P2YR subtype (i.e. $P2Y_{12}R$) were detected in the rat neuronal cell line PC12.

Embodiment 6: The Inhibition Effect of the Active Substances on Calcium Signals

1. The P2R-Correlated Calcium Signals Detected in the Cell Lines:

The rat pheochromocytoma cell line PC12, human neuroblastoma cell line SH-SY5Y and human osteosarcoma cell line HOS were filled with Fura-2 calcium ion-sensitive fluorescent dye to detect the intracellular free calcium-ion concentration. Furthermore, the P2R on the cell membrane was stimulated using ATP to observe the variations of the intracellular free calcium-ion concentration. FIGS. 3(A), 3(B) and 3(C) show the variations of the calcium signals of the receptors in (A) human osteosarcoma HOS cells, (B) rat pheochromocytoma PC12 cells and (C) human neuroblastoma SH-SY5Y cells after being stimulated with 0.1 mM ATP. The intracellular free calcium-ion concentration in human neuroblastoma SH-SY5Y cells did not vary. To exclude the possibility that cells do not generate bio-molecules which are correlated to calcium-ion signals, the acetylcholine receptor on the human neuroblastoma SH-SY5Y cells was further stimulated with 0.1 mM carbachol to confirm that the cells do have molecules which are correlated to calcium-ion signals, and the results are shown in FIG. 3(C).

2. Calcium Signals Correlated to the Individual P2R Subtypes:

Comparing the P2R-correlated calcium signals in three cell lines stimulated with ATP, the variation of the calcium-ion concentration in human osteosarcoma HOS cells was the most significant, and thus the influence of the agent on P2R can clearly be determined. Therefore, human osteosarcoma HOS cells were selected as the sample to further detect the P2R subtypes which may be correlated with calcium signals in human osteosarcoma HOS cells. The 2-methylene ATP (2-MeATP, the selective stimulator for the $P2X_1R$ and $P2X_5R$ subtypes), $\alpha,\beta$-methylene ATP ($\alpha,\beta$-MeATP, the selective stimulator for the $P2X_7$ subtype), 2-(methylthio) adenosine 5'-triphosphate (2-MeSATP, the selective stimulator for the $P2X_1$ subtype) and cytosine 5'-triphosphate (CTP, the selective stimulator for the $P2X_4$ subtype) were used to determine the P2R subtypes in human osteosarcoma HOS cells. The curves from left to right in FIG. 4 are the calcium-ion signals induced by the specific stimulators (CTP, 2-MeATP, $\alpha,\beta$-MeATP and 2-MeSATP) for the subtype receptors, indicating that at least the calcium signals correlated with $P2X_1$, $P2X_4$, $P2X_5$ and $P2Y_7$ can be detected in human osteosarcoma HOS cells, and the reaction for $P2X_4$ is the most significant.

The P2Y receptor is correlated with the G-protein (Gq). The Gq can be activated after stimulating the receptor, to further activate phospholipase C so as to generate inositol 1,4,5-trisphosphate (IP3) and release calcium ions from the IP3-sensitive calcium pool in the cell. Therefore, the remaining calcium ions in the buffer in the experiment can be chelated when using a calcium ion-free buffer supplemented with an adequate amount of EGTA, so that no extracellular calcium ions can flow into the cells. On this condition, the intracellular free calcium-ion concentration was determined to indicate that the calcium ions are released from the calcium pool in the cell. FIGS. 5(A) and 5(B) show the calcium signals correlated with the P2Y receptor, wherein FIG. 5(A) shows that the calcium signals are induced by using ATP to stimulate the P2R in a calcium ion free buffer, and this is a response for the P2R receptor-correlated calcium signals because no extracellular calcium ions flow into the cells; and FIG. 5(B) shows the calcium signals induced using the uridine triphosphate (UTP) to stimulate cells. It is shown in FIGS. 5(A) and 5(B) that at least the $P2Y_2R$- and $P2Y_4R$-correlated calcium signals can be detected in human osteosarcoma HOS cells.

Figure 6:
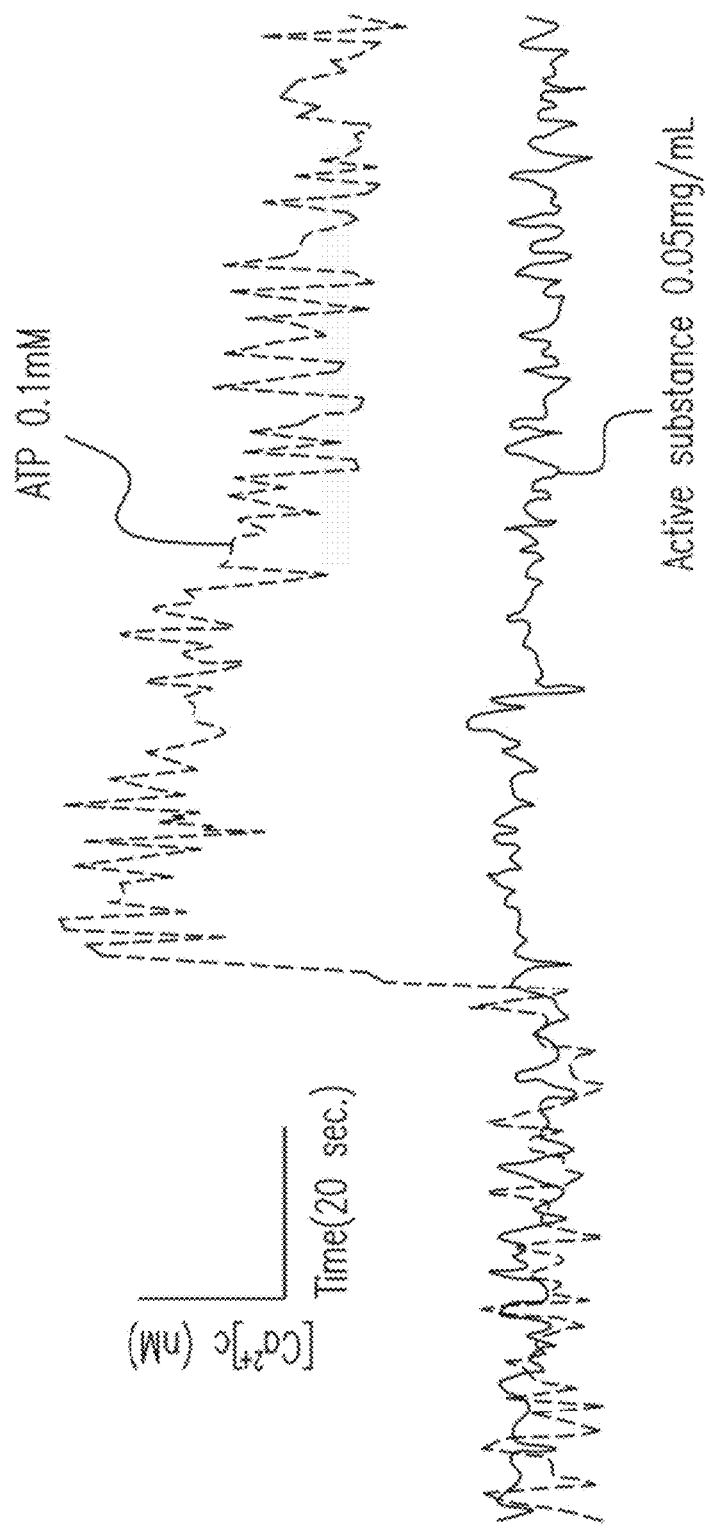
FIG. 6 shows the effect of the *H. erinaceus* mycelia alcohol extract on the ATP-stimulated P2R's calcium signals in the human osteosarcoma HOS cells according to Item 3 in Embodiment 6.

3. The P2R-Correlated Calcium Signals Inhibited by the Active Substances of *H. erinaceus*:

ATP is a stimulator for P2R in the body, and thus 0.1 mM ATP is used to stimulate the P2R receptor. The *H. erinaceus* alcohol extract was added before the calcium signals were induced using ATP to stimulate the P2R. A secondary signal is equivalent to a physiological reaction after a receptor is stimulated. Therefore, it can be seen in FIG. 6 that the P2R's calcium signals induced by ATP are completed inhibited, and it is proved that P2R's functions can be inhibited by the *H. erinaceus* alcohol extract. It is proved in the above experiments that there are a variety of P2XRs and P2YRs on the HOS cells and the functions of the P2R receptors can be completely inhibited by the *H. erinaceus* alcohol extract, and it is determined that the *H. erinaceus* alcohol extract has an inhibition effect on receptors such as $P2X_1$, $P2X_4$, $P2X_5$, $P2Y_7$, $P2Y_2$, $P2Y_4$ receptors and so on.

Figure 7A:
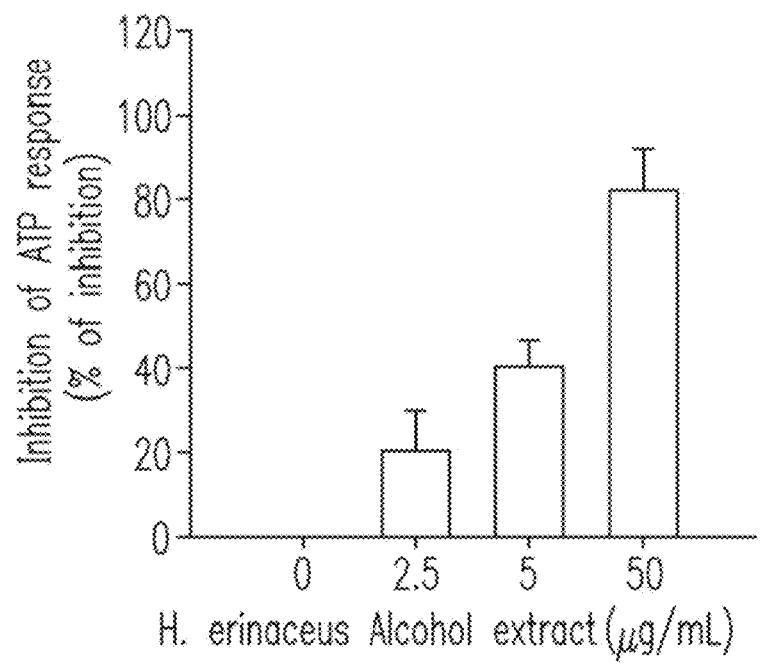
FIGS. 7(A) and 7(B) show the inhibition effect of the calcium signals induced by (A) the alcohol extract and (B)
Figure 7B:
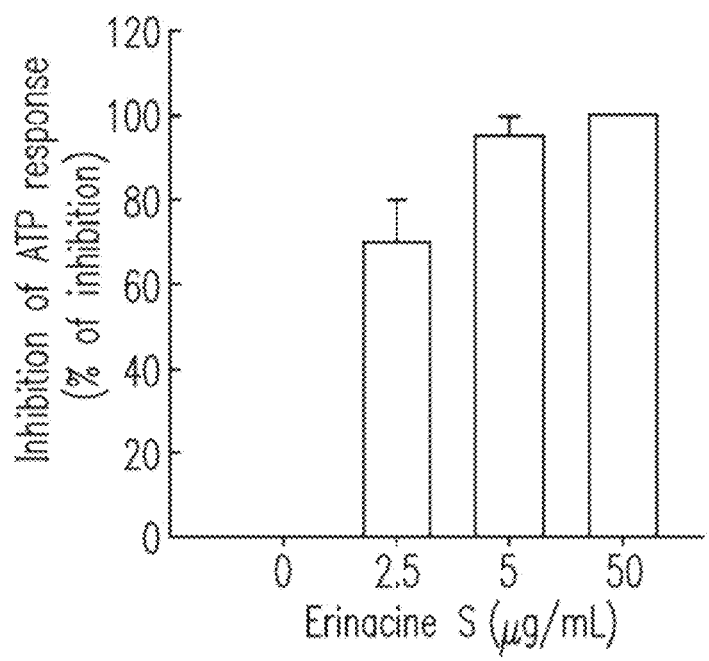

4. The Correlation Between the Inhibition Functions of the *H. erinaceus* Active Substances and the Erinacine S and their Concentrations:

FIGS. 7(A) and 7(B) show the inhibition effect of (A) the *H. erinaceus* alcohol extract of 2.5, 5 and 50 μg/ml and (B) the erinacine S of 5, 10 and 15 μg/ml on the variation of the intracellular calcium-ion concentration in human osteosarcoma HOS cells induced using the ATP to stimulate the P2R receptor, and the inhibition effect is more significant in a dosage-dependent manner, indicating that the dosage given is correlated with the inhibition effect.

Embodiment 7: The Determination of the Effect that the *H. erinaceus* Active Substances Reduce Animals' Pain This embodiment was performed to observe the mice's pain reaction to the extrinsic stimulation before/after administration via the tail flick test and the hot-plate test, after the mice were administered with the *H. erinaceus* active substances (i.e. the alcohol extract obtained in Embodiment 2 and the alcohol extraction mixture obtained in Embodiment 3) for a short term or a long term.

1. The Tail Flick Test after the *H. erinaceus* Active Substances were Administered for a Short Term:

Mice in this experiment were divided into three groups, i.e. the control group, the *H. erinaceus* mycelia/alcohol extract (the alcohol extraction mixture group), and the *H. erinaceus* alcohol extract (the alcohol extract group). Each group had five male C57BL/6 Narl mice which were older than eight weeks old. The mice were orally administered with 2500 mg/kg of drugs via a soft feeding tube, and the mice in the control group were fed with an equal amount of water. The mouse's nociception was determined by the tail flick test before administration, and 30 and 60 minutes after administration. The experimental results were expressed as mean±standard deviation, and the significance of statistics among the alcohol extraction mixture group, the alcohol extract group and the control group was analyzed using Student's t-test. Therefore, the pain-relieving effect of administering the active substances for a short term can be observed, and the results are shown in FIG. 8.

The tail-flick basic values were examined before administration, the tail-flick reaction time in three groups was 4.1±1.5 seconds (s) in the control group, 4.3±1.9 s in the alcohol extraction mixture group, and 4.5±1.2 s in the alcohol extract group. The p-value for Student's t-test between the alcohol extraction mixture group and the control group was 0.8, the p-value for Student's t-test between the alcohol extract group and the control group was 0.6, and the p-value for Student's t-test between the alcohol extraction mixture group and the alcohol extract group was 0.8, indicating that there was no significant difference between groups before administration.

The mouse's nociception reaction was determined by the tail flick test 30 minutes after administration. The experimental results show that the tail flick reaction time was 2.0±0.5 s in the control group, 6.2±1.6 s in the alcohol extraction mixture group, and 8.4±1.1 s in the alcohol extract group. The p-value for Student's t-test between the alcohol extraction mixture group and the control group was 0.0008 with a significant difference, the p-value for Student's t-test between the alcohol extract group and the control group was 0.000009 with a significant difference, and the p-value for Student's t-test between the alcohol extraction mixture group and the alcohol extract group was 0.07 without a significant difference.

The mouse's nociception reaction was determined by the tail flick test 60 minutes after administration. The experimental results showed that the tail-flick reaction time was 2.1±0.57 s in the control group, 5.7±2.46 s in the alcohol extraction mixture group, and 7.2±1.9 s in the alcohol extract group. The p-value for Student's t-test between the alcohol extraction mixture group and the control group was 0.0256 with a significant difference, the p-value for Student's t-test between the alcohol extract group and the control group was 0.0016 with a significant difference, and the p-value for Student's t-test between the alcohol extraction mixture group and the alcohol extract group was 0.33 without a significant difference.

2. The Difference in the Tail Flick Test Before/after Administration with the *H. erinaceus* Active Substances for a Short Term:

The experimental conditions are similar to the condition in the subsection "1. The tail flick test after the *H. erinaceus* active substances was administered for a short term", and the difference of the tail-flick reaction times among the alcohol extract group, the alcohol extraction mixture group and the control group was compared. Therefore, the pain-relieving effect of administering the active substances for a short term can be observed, and the results are shown in FIG. 9.

The mouse's nociception reaction was determined by the tail flick test 30 minutes after administration. The experimental results show that the tail-flick reaction time in the control group was shorter compared to the tail–flick basic value before administration, with a difference of −2.1±1.7 s; the tail-flick reaction time in the alcohol extraction mixture group was longer compared to that before administration, with a difference of 2.6±2.18 s; and the tail-flick reaction time in the alcohol extract group was longer compared to that before administration, with a difference of 3.9±1.61 s. The p-value for Student's t-test between the alcohol extraction mixture group and the control group was 0.008 with a significant difference, the p-value for Student's t-test between the alcohol extract group and the control group was 0.00108 with a significant difference, and the p-value for Student's t-test between the alcohol extraction mixture group and the alcohol extract group was 0.35 without a significant difference.

The mouse's nociception reaction was determined by the tail flick test 60 minutes after administration. The experimental results show that the tail-flick reaction time in the control group was shorter compared to the tail-flick basic value before administration, with a difference of −1.0±0.71 s; the tail-flick reaction time in the alcohol extraction mixture group was longer compared to that before administration, with a difference of 2.0±2.53 s; and the tail-flick reaction time in the alcohol extract group was longer compared to that before administration, with a difference of 2.6±1.77 s. The p-value for Student's t-test between the alcohol extraction mixture group and the control group was 0.033 with a significant difference, the p-value for Student's t-test between the alcohol extract group and the control group was 0.0028 with a significant difference, and the p-value for Student's t-test between the alcohol extraction mixture group and the alcohol extract group was 0.66 without a significant difference.

3. The Maximum Possible Effects in the Tail Flick Test after Administration of the *H. erinaceus* Active Substances for a Short Term The conditions of this experiment are similar to those in the subsection "1. The tail flick test after the *H. erinaceus* active substances was administered for a short term" above, and the maximum possible effects (MPE) are calculated as follows. The tail-flick reaction time after administration minus the tail-flick reaction time before administration (a tail-flick basic value for a single mouse) have a difference, and then the difference divided by the tail-flick basic value for this single mouse is the MPE. Therefore, the pain-relieving effect of administering the active substances for a short term can be observed, and the results are shown in FIG. 10.

The mouse's nociception reaction was determined by the tail flick test 30 minutes after administration. The experimental results show that the tail-flick reaction time in the control group was shorter (about half) compared to the tail-flick basic value before administration; the tail-flick reaction time in the alcohol extraction mixture group was longer compared to that before administration; and the tail-flick reaction time in the alcohol extract group was longer by about one time compared to that before administration. The p-value for Student's t-test between the alcohol extraction mixture group and the control group was 0.03 with a significant difference, the p-value for Student's t-test between the alcohol extract group and the control group was 0.0134 with a significant difference, and the p-value for Student's t-test between the alcohol extraction mixture group and the alcohol extract group was 0.31 without a significant difference.

The mouse's nociception reaction was determined by the tail flick test 60 minutes after administration. The experimental results show that the tail-flick reaction time in the control group was shorter compared to the tail-flick basic value before administration; the tail-flick reaction time in the alcohol extraction mixture group was longer by about one time compared to that before administration; and the tail-flick reaction time in the alcohol extract group was longer compared to that before administration. The p-value for Student's t-test between the alcohol extraction mixture group and the control group was 0.05 with a significant difference, the p-value for Student's t-test between the alcohol extract group and the control group was 0.004 with a significant difference, and the p-value for Student's t-test between the alcohol extraction mixture group and the alcohol extract group was 0.61 without a significant difference. It is predicted that the *H. erinaceus* active substances have an immediate pain-relieving effect which can at least continue for about 60 minutes.

4. The Hot-Plate Test after Administration of the *H. erinaceus* Active Substances for a Long Term:

This assay is used to determine whether the administration of the *H. erinaceus* active substances for a long term can delay in response caused by the hot plate. Each mouse was fed with 2500 mg/kg active substance for three days, and the interval between two feeds was 24 hours. Next, the hot-plate test was performed after feeding the active substances for three days, the amounts of paw lifting, licking or jumping were determined and the results are shown in FIG. 11.

After administration for three days, the experimental results show that the paw withdrawal reaction time was 6.4±1.8 s in the control group, 11.7±2.5 s in the alcohol extraction mixture group, and was 11.5±1.8 s in the alcohol extract group. The p-value for Student's t-test between the alcohol extraction mixture group and the control group was 0.005 with a significant difference, the p-value for Student's t-test between the alcohol extract group and the control group was 0.0025 with a significant difference, and the p-value for Student's t-test between the alcohol extraction mixture group and the alcohol extract group was 0.09 without a significant difference.

30 minutes after performing the first-time hot-plate test on administration day 3, the paw withdrawal reaction time was determined again with the same experimental method. The experimental results show that the paw withdrawal reaction time was 6.3±0.8 s in the control group, 11.8±2.5 s in the alcohol extraction mixture group, and was 8.9±1.2 s in the alcohol extract group. The p-value for Student's t-test between the alcohol extraction mixture group and the control group was 0.007 with a significant difference, the p-value for Student's t-test between the alcohol extract group and the control group was 0.010 with a significant difference, and the p-value for Student's t-test between the alcohol extraction mixture group and the alcohol extract group was 0.09 without significant difference.

After calculating the first-determination data after feeding for 3 days and the data from the after-30-minutes determination, the experimental results show that the paw withdrawal reaction time was 5.7±2.4 sin the control group, 11.7±2.3 s in the alcohol extraction mixture group, and was 10.3±2.0 s in the alcohol extract group. The p-value for Student's t-test between the alcohol extraction mixture group and the control group was 0.00006 with a significant difference, the p-value for Student's t-test between the alcohol extract group and the control group was 0.0003 with a significant difference, and the p-value for Student's t-test between the alcohol extraction mixture group and the alcohol extract group was 0.81 without a significant difference.

According to this animal experiment, it can be seen that the alcohol extraction mixture and the alcohol extract have significant pain-relieving effects on a short-term reaction after a 30-minute administration, and the pain-relieving effect tended to decline after a 60-minute administration. In the experiment where the alcohol extraction mixture and alcohol extract were fed for a long term, deallergization occurs and the pain-relieving effect tends to stabilize.

In conclusion, the *H. erinaceus* active substances including the *H. erinaceus* mycelia, the *H. erinaceus* alcohol extract, the *H. erinaceus* alcohol extraction mixture and the erinacine S disclosed in the present invention have been proven to have the pain-relieving effect, and can be widely used for pain relief.

The invention claimed is:

1. A method for relieving pain in a subject suffering from neuropathic pain or cancer pain, comprising:
providing a pharmaceutical composition comprising an effective amount of an active substance of *Hericium erinaceus* (*H. erinceus*) mycelium, wherein the active substance is a heripene having formula (I) as follows:

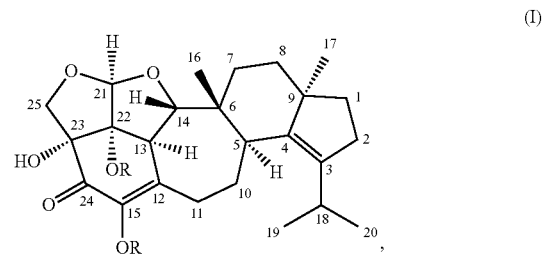

(I)

where R is selected from the group consisting of hydrogen, hydroxyl, $C_1$-$C_{10}$ alkyl, $C_2$-$C_{10}$ alkenyl and $C_2$-$C_{10}$ alkynyl, each of which is optionally substituted with a halogen, oxygen, nitrogen, phosphorus, or sulfur; and
administering an effective amount of the pharmaceutical composition to the subject.

2. The method according to claim 1, wherein R is hydrogen.

3. The method according to claim 1, wherein the pharmaceutical composition further comprises a component selected from the group consisting of a biologically acceptable carrier, an excipient, a diluent and an adjuvant.

4. The method according to claim 1, wherein the active substance of the *H. erinaceus* mycelium is obtained by the method comprising:
(a) inoculating and incubating the *H. erinaceus* mycelium to provide an inoculated and incubated *H. erinaceus* mycelium on an agar plate;
(b) inoculating and incubating the inoculated and incubated *H. erinaceus* mycelium obtained in step (a) in a first medium on a small scale to provide a second inoculated and incubated *H. erinaceus* mycelium; and
(c) inoculating and incubating the second inoculated and incubated *H. erinaceus* mycelium obtained in step (b) in a second medium on a large scale to obtain a fermented medium containing the active substance.

5. The method according to claim 4, wherein the *H. erinaceus* is incubated in step (a) at 15-32° C. for 8-16 days.

6. The method according to claim 4, wherein the *H. erinaceus* is incubated in step (b) at 20-30° C., pH 4.5-6.5, and a shaking rate of 100-250 rounds per minutes (rpm) for 3-5 days.

7. The method according to claim 4, wherein in step (c), the second medium on the large scale is in a fermentation tank having a tank pressure of 0.8-1.2 $kg/cm^2$ and a stirring rate of 10-150 rpm; a gas is introduced into the fermentation tank at an aeration rate of 0.5-1 volume per volume per minute (vvm), wherein the gas is selected from a group consisting of air, oxygen, carbon dioxide, nitrogen gas or a combination thereof; and the incubation is performed at 24-32° C. and pH 4.5-5.5 for 8-16 days.

8. The method according to claim 4, wherein the first medium and the second medium are the same.

9. The method according to claim 8, wherein each of the first medium and the second medium comprises a complex carbon and nitrogen source, animal or plant sources of a protein or a hydrolyzate thereof, an inorganic salt, a saccharide, a yeast extract, a malt extract, a defoaming agent or a combination thereof, and wherein the complex carbon and nitrogen source is a grain or a legume, and the inorganic salt is a sulfate or a phosphate.

10. The method according to claim 4, wherein the preparation method further comprises (d) desiccating the fermented medium to obtain a powder.

11. The method according to claim 10, wherein the active substance of the *H. erinaceus* is isolated from the powder.

12. The method according to claim 10, wherein the powder is further extracted with an alcohol solution to obtain an alcohol extract, wherein the alcohol solution is an ethanol solution of 30-100 volume-volume percentage (v/v%) or a methanol solution of 30-100 (v/v%).

13. The method according to claim 12, wherein the alcohol extract is further extracted with water-ethyl, followed by a column chromatography to obtain the active substance.

14. The method according to claim 12, wherein the stereocenters of the formula (I) at C-5, C-6, C-9, C-13, C-14, C-21, C22 and C-23 are one of an R configuration and an S configuration.

15. The method according to claim 14, wherein the heripene is erinacine S having formula (II) as follows:

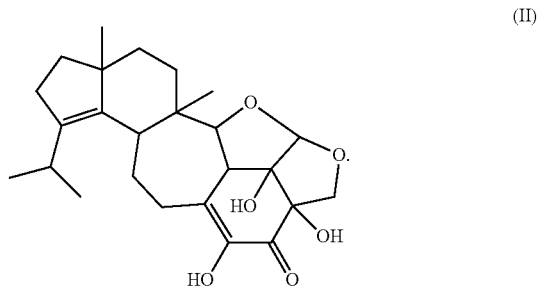

(II)

* * * * *